US012611222B2

(12) United States Patent
Morisaki et al.

(10) Patent No.: US 12,611,222 B2
(45) Date of Patent: Apr. 28, 2026

(54) ULTRASONIC TREATMENT INSTRUMENT

(71) Applicant: OLYMPUS MEDICAL SYSTEMS CORP., Tokyo (JP)

(72) Inventors: Kazuhiro Morisaki, Yokohama (JP); Ojiro Kitamura, Hachioji (JP); Kazue Tanaka, Sagamihara (JP); Tsunetaka Akagane, Hachioji (JP); Fumiya Ishikawa, Hachioji (JP); Koichi Tsuruta, Yokohama (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 222 days.

(21) Appl. No.: 18/454,540

(22) Filed: Aug. 23, 2023

(65) Prior Publication Data

US 2023/0397924 A1      Dec. 14, 2023

Related U.S. Application Data

(63) Continuation of application No. PCT/JP2021/007919, filed on Mar. 2, 2021.

(51) Int. Cl.
*A61B 17/32* (2006.01)

(52) U.S. Cl.
CPC .................. *A61B 17/320092* (2013.01); *A61B 2017/320082* (2017.08); *A61B 2017/320094* (2017.08)

(58) Field of Classification Search
CPC .................. A61B 17/29; A61B 17/295; A61B 17/320092; A61B 2017/2825;
(Continued)

(56) References Cited

U.S. PATENT DOCUMENTS 6,193,709 B1 *   2/2001   Miyawaki ...... A61B 17/320092
                                                    606/49
2004/0186463 A1 *   9/2004   Murakami ............... A61N 7/02
                                                    606/27
(Continued)

FOREIGN PATENT DOCUMENTS

JP        2009514566 A        4/2009
JP        2016538068 A        12/2016
(Continued)

OTHER PUBLICATIONS

"International Application Serial No. PCT/JP2021/007919, International Search Report dated May 11, 2021", (May 11, 2021), 4 pgs.

*Primary Examiner* — Robert A Lynch
(74) *Attorney, Agent, or Firm* — Schwegman Lundberg & Woessner, P.A.

(57)      ABSTRACT

An ultrasonic treatment instrument includes: a vibration transmitter including a treatment portion for treating a living tissue at a distal end of the vibration transmitter, the vibration transmitter being configured to transfer ultrasonic vibration from a proximal end of the vibration transmitter toward the treatment portion; a holder configured to open and close with respect to the treatment portion; a resin pad including a gripping surface for gripping the living tissue between the resin pad and the treatment portion; and a heat transmitter that is configured separately from the holder and extends from the holder to an inside of the resin pad.

11 Claims, 38 Drawing Sheets

(58) Field of Classification Search
CPC ....... A61B 2017/320078; A61B 2017/320082;
A61B 2017/320088; A61B 2017/320094;
A61B 2017/320095; A61B 18/1442;
A61B 18/1445; A61B 2018/00095; A61B
2018/00595; A61B 2018/00994
See application file for complete search history.

(56) References Cited

U.S. PATENT DOCUMENTS

| | | | |
|---|---|---|---|
| 2007/0191713 A1* | 8/2007 | Eichmann .......... | A61B 17/1606 |
| | | | 600/471 |
| 2015/0148833 A1 | 5/2015 | Stokes et al. | |
| 2016/0235432 A1* | 8/2016 | Akagane ............ | A61B 18/1442 |
| 2017/0000556 A1* | 1/2017 | Morisaki ............ | A61B 18/1206 |
| 2017/0252098 A1* | 9/2017 | Nagata ............... | A61B 18/1442 |
| 2018/0042638 A1* | 2/2018 | Hirai .............. | A61B 17/320092 |
| 2019/0046226 A1* | 2/2019 | Yasunaga ........... | A61B 17/3205 |
| 2019/0142505 A1* | 5/2019 | Morisaki .............. | A61B 18/085 |
| | | | 606/51 |

FOREIGN PATENT DOCUMENTS

| | | | |
|---|---|---|---|
| KR | 20180063493 A | 6/2018 | |
| WO | WO-2016175038 A1 | 11/2016 | |
| WO | WO-2018011918 A1 | 1/2018 | |
| WO | WO-2018011920 A1 | 1/2018 | |

* cited by examiner

ULTRASONIC TREATMENT INSTRUMENT

CROSS-REFERENCE TO RELATED APPLICATION

This application is a continuation of International Application No. PCT/JP2021/007919, filed on Mar. 2, 2021, the entire contents of which are incorporated herein by reference.

BACKGROUND

1. Technical Field

The present disclosure relates to an ultrasonic treatment instrument.

2. Related Art

In the related art, there has been known an ultrasonic treatment instrument that treats a treatment target site (hereinafter, referred to as a target site) in a living tissue by applying ultrasonic energy to the target site (see, for example, WO 2018/011918A).

The ultrasonic treatment instrument described in WO 2018/011918A includes a rod, a holder, and a pad (hereinafter, referred to as a resin pad) described below.

The rod includes a treatment portion for treating a living tissue at a distal end, and transfers ultrasonic vibration from a proximal end toward the treatment portion.

The holder opens and closes with respect to the treatment portion.

The resin pad is held with respect to the holder, and has an abutment surface that grips the living tissue between the resin pad and the treatment portion.

SUMMARY

In some embodiments, an ultrasonic treatment instrument includes: a vibration transmitter including a treatment portion for treating a living tissue at a distal end of the vibration transmitter, the vibration transmitter being configured to transfer ultrasonic vibration from a proximal end of the vibration transmitter toward the treatment portion; a holder configured to open and close with respect to the treatment portion; a resin pad including a gripping surface for gripping the living tissue between the resin pad and the treatment portion; and a heat transmitter that is configured separately from the holder and extends from the holder to an inside of the resin pad.

In some embodiments, an ultrasonic treatment instrument includes: a vibration transmitter including a treatment portion for treating a living tissue at a distal end of the vibration transmitter, and the vibration transmitter being configured to transfer ultrasonic vibration from a proximal end of the vibration transmitter toward the treatment portion; a holder configured to open and close with respect to the treatment portion; a resin pad including a gripping surface for gripping the living tissue between the resin pad and the treatment portion; and a heat transmitter disposed between the holder and the resin pad.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 35 is a view illustrating Modification 7-3 of the first to sixth embodiments;

FIG. 36 is a view illustrating Modification 7-4 of the first to sixth embodiments;

DETAILED DESCRIPTION

Figure 1:
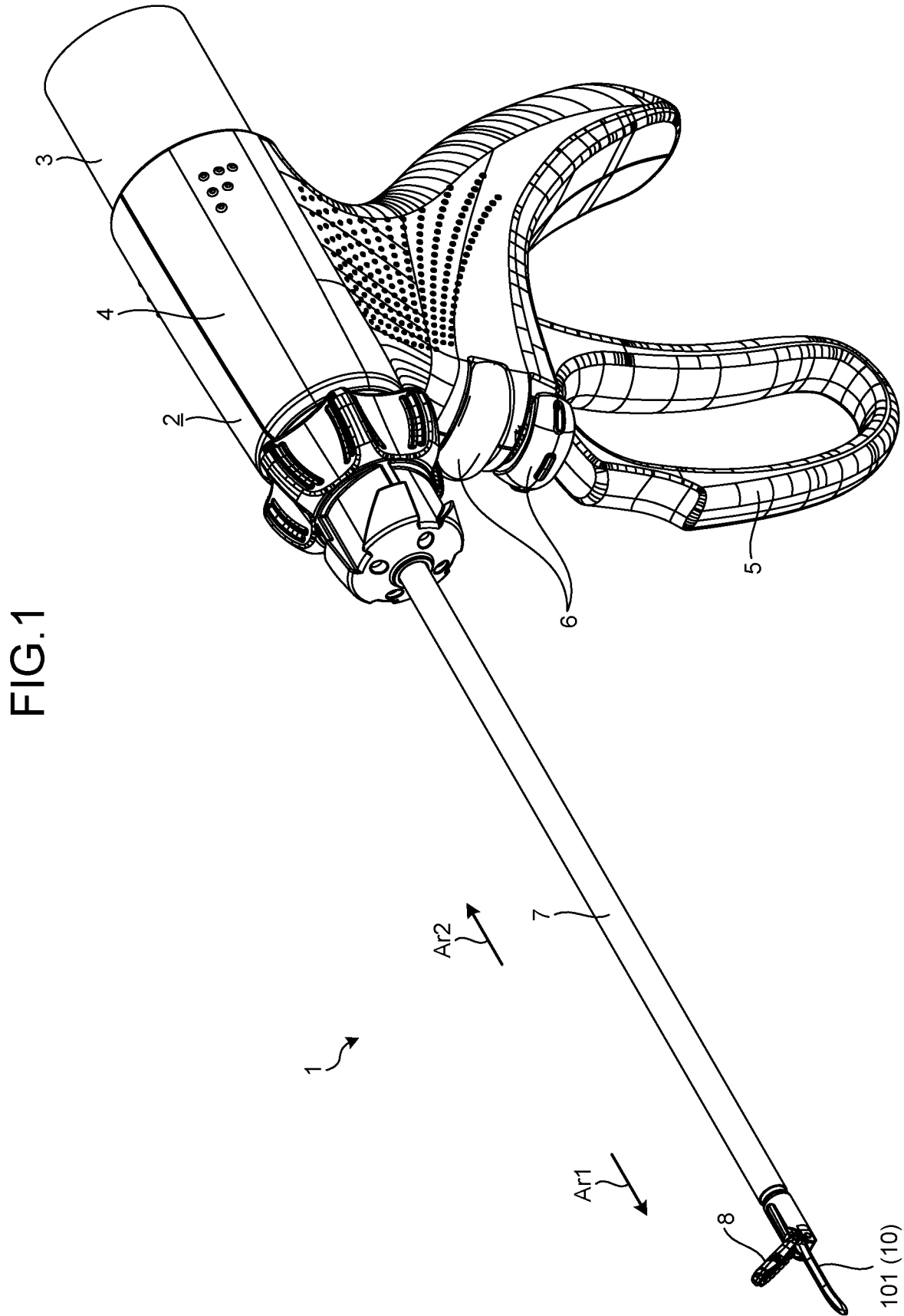
FIG. 1 is a view illustrating an ultrasonic treatment instrument according to a first embodiment.

Hereinafter, modes for carrying out the disclosure (hereinafter, embodiments) will be described with reference to the drawings. The disclosure is not limited by the embodiments described below. Furthermore, in the description of the drawings, the same portions are denoted by the same reference numerals.

First Embodiment

Schematic Configuration of Ultrasonic Treatment Instrument

Figure 2:
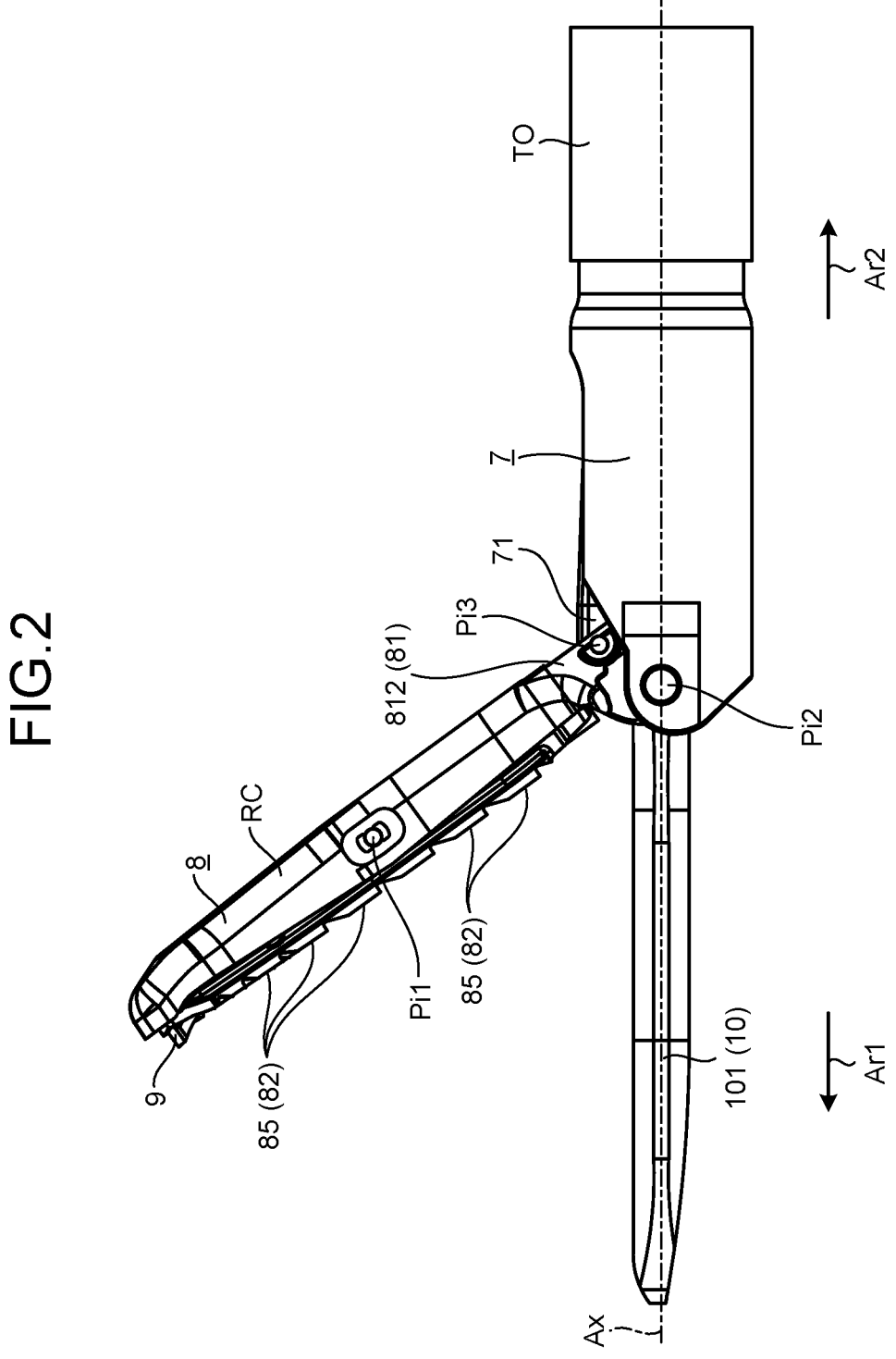
FIG. 2 is a view illustrating a distal end portion of the ultrasonic treatment instrument.
Figure 3:
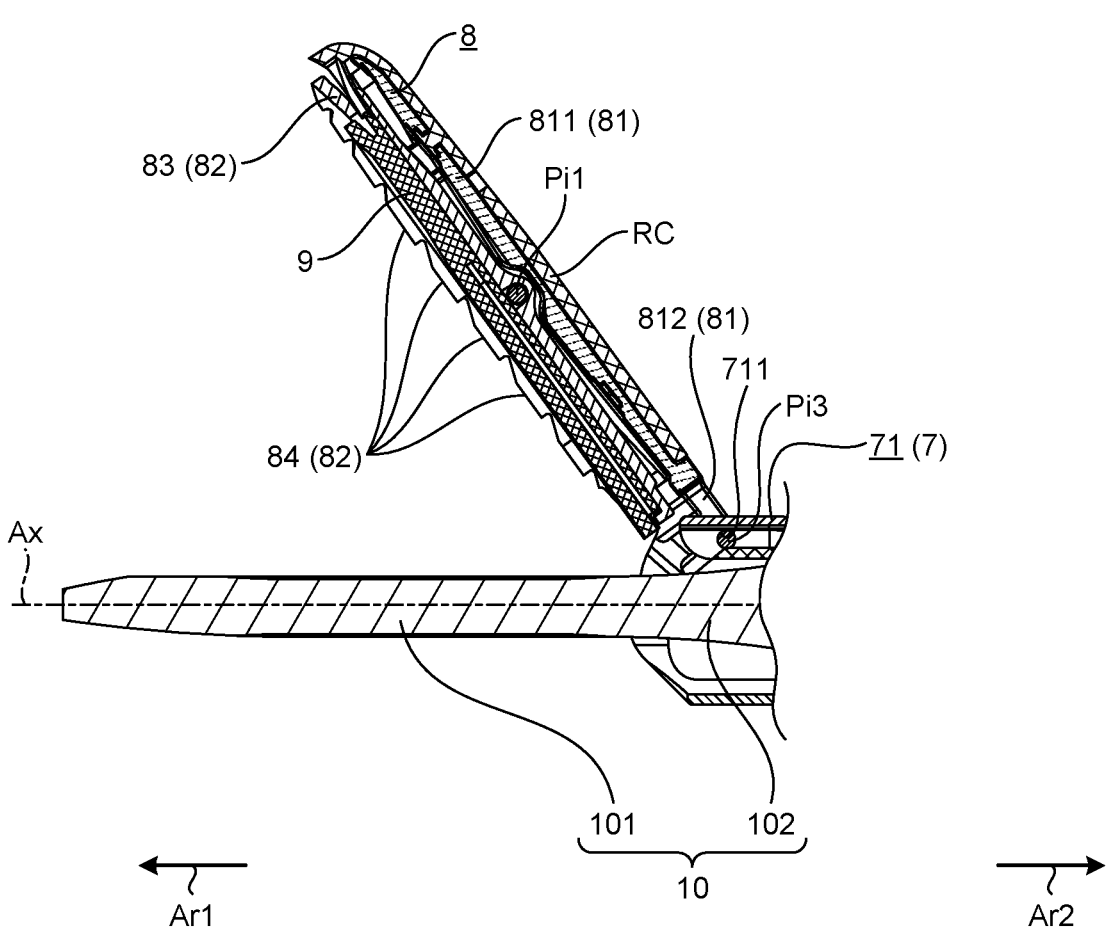
FIG. 3 is a view illustrating a distal end portion of the ultrasonic treatment instrument.

FIG. 1 is a view illustrating an ultrasonic treatment instrument 1 according to a first embodiment. FIGS. 2 and 3 are views illustrating a distal end portion of the ultrasonic treatment instrument 1. Specifically, FIG. 2 is a view of the distal end portion of the ultrasonic treatment instrument 1 viewed along a normal direction of a plane including a central axis Ax of a sheath 7 in a state where a jaw 8 and a vibration transmitter 10 are included in the plane. FIG. 2 is a cross-sectional view of the distal end portion of the ultrasonic treatment instrument 1 cut along the plane including the central axis Ax of the sheath 7 in a state where the jaw 8 and the vibration transmitter 10 are included in the plane. A "width direction" described below means a direction orthogonal to paper surfaces of FIGS. 2 and 3.

The ultrasonic treatment instrument 1 applies ultrasonic energy and high-frequency energy to a treatment target site (hereinafter, referred to as a target site) in a living tissue to treat the target site. Here, the treatment means, for example, coagulation and incision of the target site. As illustrated in FIG. 1, the ultrasonic treatment instrument 1 includes a handpiece 2 and an ultrasonic transducer 3.

As illustrated in FIGS. 1 to 3, the handpiece 2 includes a holding case 4 (FIG. 1), an operation handle 5 (FIG. 1), a switch 6 (FIG. 1), a sheath 7, a jaw 8, a resin pad 9 (FIGS. 2 and 3), and a vibration transmitter 10.

The holding case 4 supports the entire ultrasonic treatment instrument 1.

The operation handle 5 is movably attached to the holding case 4 and receives an opening/closing operation by an operator.

The switch 6 is provided in a state of being exposed to an outside of the holding case 4, and receives an output start operation by the operator. Then, the switch 6 outputs an operation signal corresponding to the output start operation to a control device (not illustrated) electrically coupled to the ultrasonic treatment instrument 1.

The sheath 7 has a substantially cylindrical shape as a whole. Hereinafter, one side along the central axis Ax of the sheath 7 is referred to as a distal end side Ar1 (FIGS. 1 to 3), and the other side is referred to as a proximal end side Ar2 (FIGS. 1 to 3). Then, the sheath 7 is attached to the holding case 4 by inserting a portion of the proximal end side Ar2 into the holding case 4 from the distal end side Ar1 of the holding case 4.

Figure 35:
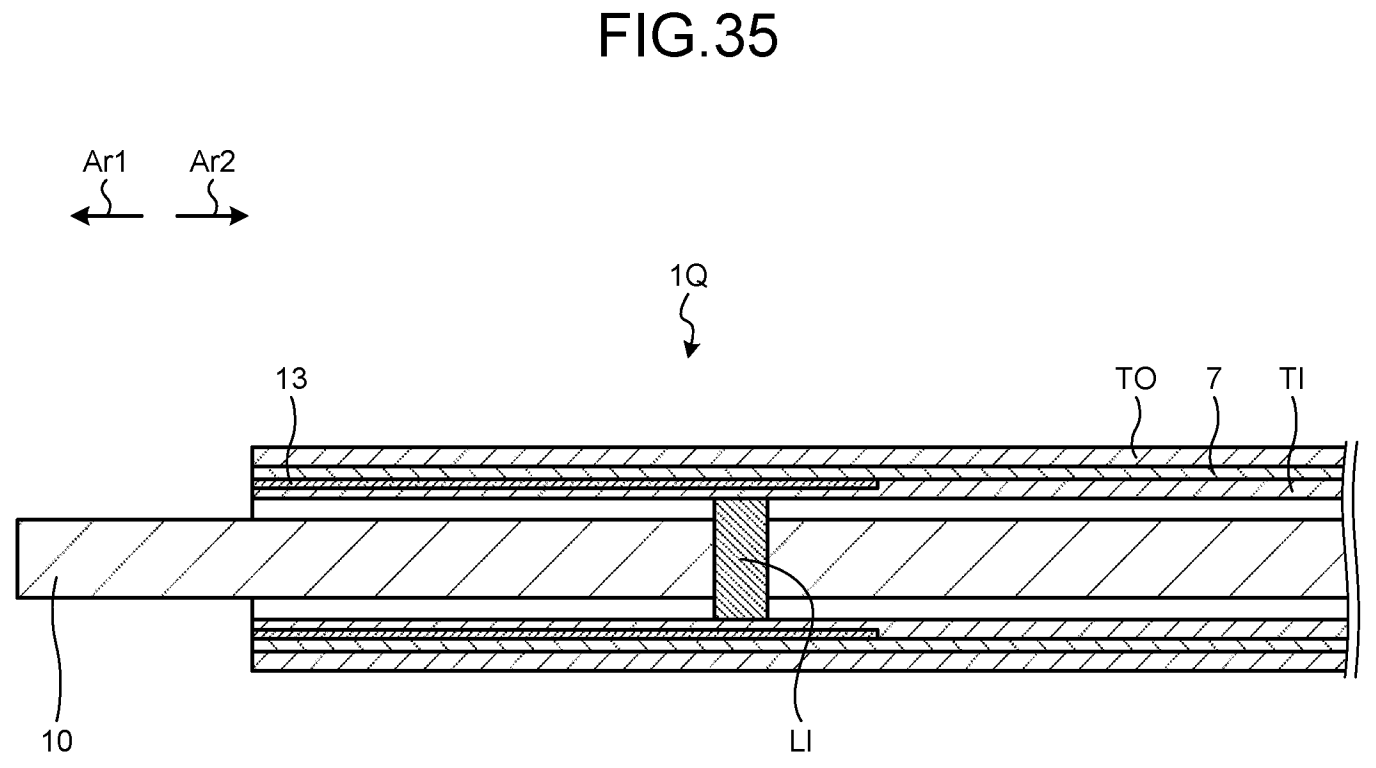
Figure 36:
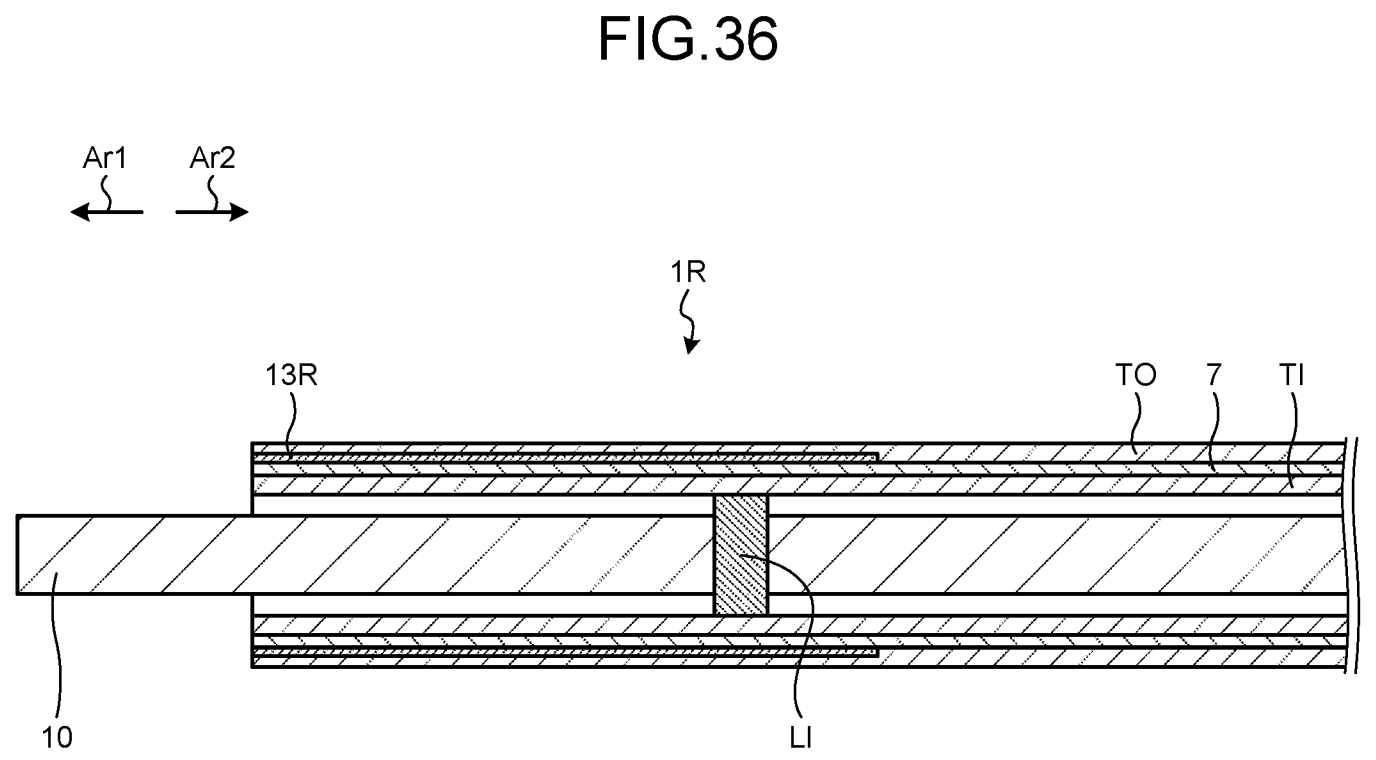

In the sheath 7, an outer peripheral surface is covered with an electrically insulating outer tube TO (see FIGS. 35 and 36).

In addition, in the sheath 7, an inner peripheral surface is covered with an electrically insulating inner tube TI (see FIGS. 35 and 36).

In the following description of the configuration of the jaw 8 and the resin pad 9, a side away from a treatment portion 101 configuring the vibration transmitter will be referred to as a back surface side Ar3 (see FIGS. 4 to 9), and a side close to the treatment portion 101 will be referred to as a treatment portion side Ar4 (see FIGS. 4 to 9).

Figure 4:
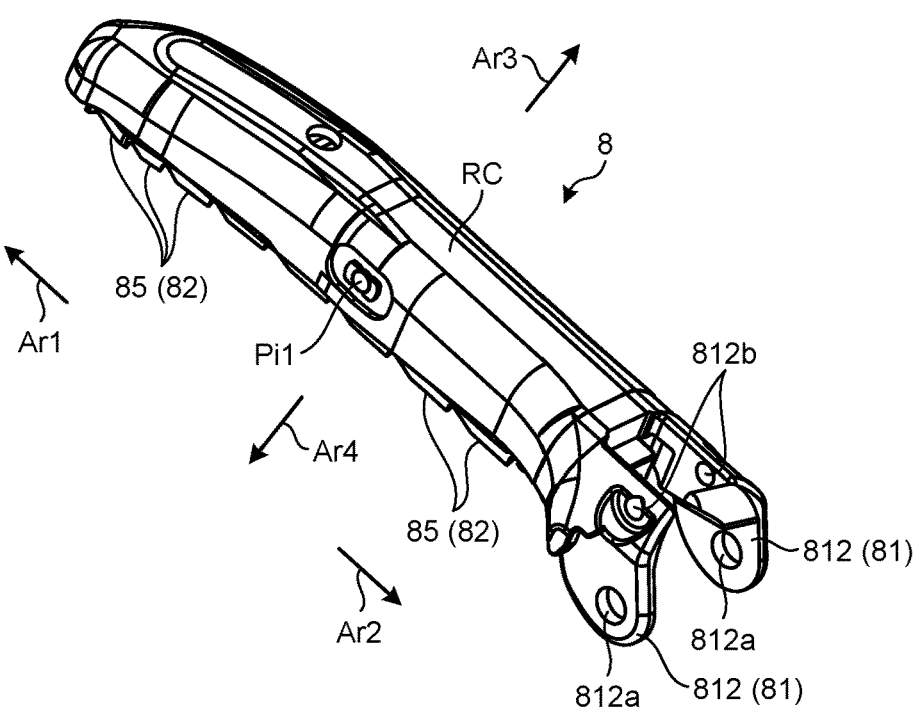
FIG. 4 is a view illustrating a jaw.
Figure 5:
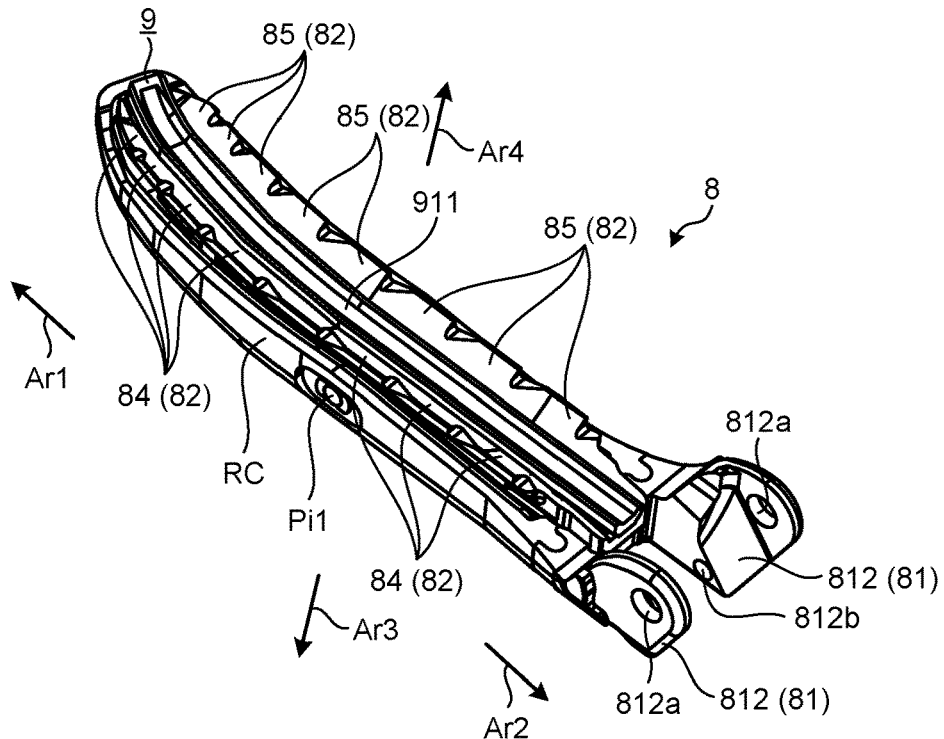
FIG. 5 is a view illustrating the jaw.

FIGS. 4 and 5 are views illustrating the jaw 8. Specifically, FIG. 4 is a perspective view of the jaw 8 as viewed from the back surface side Ar3. FIG. 5 is a perspective view of the jaw 8 as viewed from the treatment portion side Ar4. FIG. 5 illustrates a state in which the resin pad 9 is assembled to the jaw 8.

The jaw 8 corresponds to a holder. The jaw 8 can be opened and closed with respect to the treatment portion 101 (FIGS. 2 and 3) by being pivotally supported with respect to an end portion of the sheath 7 on the distal end side Ar1. Then, when the jaw 8 is closed with respect to the treatment portion 101, the target site is gripped between the resin pad 9 held by the jaw 8 and the treatment portion 101. As illustrated in FIG. 4 or 5, the jaw 8 includes an arm 81 and a wiper jaw 82.

Figure 6:
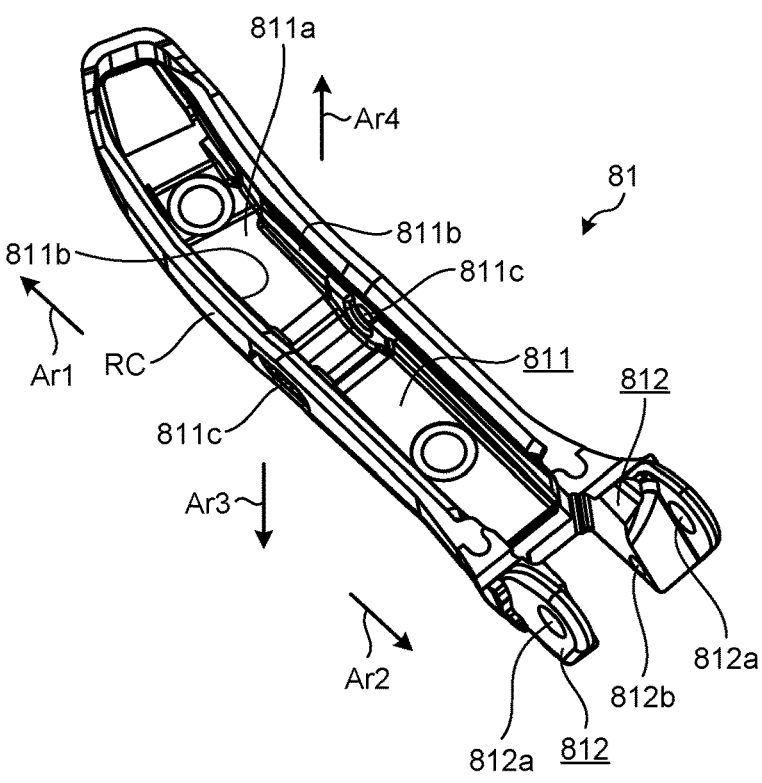
FIG. 6 is a view illustrating an arm.

FIG. 6 is a view illustrating the arm 81. Specifically, FIG. 6 is a perspective view of the arm 81 as viewed from the treatment portion side Ar4.

The arm 81 is made of an electrically conductive material. As illustrated in FIG. 6, the arm 81 is a member in which an arm body 811 and a pair of bearing portions 812 are integrally formed.

The arm body 811 is formed of a substantially long plate body. In the present first embodiment, a longitudinal direction of the arm body 811 is a direction along a curve toward a left side as it goes toward the distal end side Ar1 when viewed from the proximal end side Ar2 in a state where the jaw 8 is positioned on an upper side with respect to the treatment portion 101.

In the arm body 811, as illustrated in FIG. 6, a first recess 811a extending from the proximal end toward the distal end side Ar1 along the longitudinal direction of the arm body 811 is provided on a surface on the treatment portion side Ar4.

As illustrated in FIG. 6, first insertion holes 811c that penetrate in the width direction and through which first pins Pit (FIGS. 4 and 5) are inserted are provided respectively in side wall portions 811b on both sides of the arm body 811 constituting the first recess 811a in the width direction. The two first insertion holes 811c are positioned substantially at the center of the arm body 811 in the longitudinal direction respectively. In addition, a straight line connecting the two first insertion holes 811c is parallel to the width direction. In the present first embodiment, the first pin Pit is fixed to the arm body 811 by welding in a state of being inserted into each of the first insertion holes 811c.

In addition, an electrically insulating resin cover RC (FIGS. 4 to 6) is integrally formed on the surface of the arm body 811 on the back surface side Ar3 in a state of covering the surface of the back surface side Ar3. In the present first embodiment, the resin cover RC is insert-molded with respect to the arm body 811, but the disclosure is not limited thereto. For example, a configuration in which the resin cover RC is fixed to the arm body 811 by snap-fitting or a metal pin may be adopted.

Each of the pair of bearing portions 812 is provided at the proximal end of the arm body 811, and is formed of plate bodies facing each other in the width direction.

As illustrated in FIG. 6, each of the pair of bearing portions 812 is provided with a second insertion hole 812a that penetrates the front and back surfaces respectively and through which each of two second pins Pi2 is inserted. That is, the arm 81 is coupled to the sheath 7 by the two second pins Pi2.

In addition, as illustrated in FIG. 4, each of the pair of bearing portions 812 is provided with a third insertion hole 812b which penetrates the front and back surfaces respectively and through which a third pin Pi3 is inserted. In the present first embodiment, the third pin Pi3 is fixed to the arm 81 by welding in a state of being inserted into each of fourth insertion holes 711 (FIG. 3) and each of the third insertion holes 812b of an opening/closing mechanism 71 constituting the sheath 7. That is, the arm 81 is coupled to the opening/closing mechanism 71 by the third pin Pi3. Then, the arm 81 rotates about the two second pins Pi2 in conjunction with the movement of the opening/closing mechanism 71 to the distal end side Ar1 or the proximal end side Ar2 according to the opening and closing operation to the operation handle 5 by the operator. As a result, the jaw 8 is opened and closed with respect to the treatment portion 101.

Figure 7:
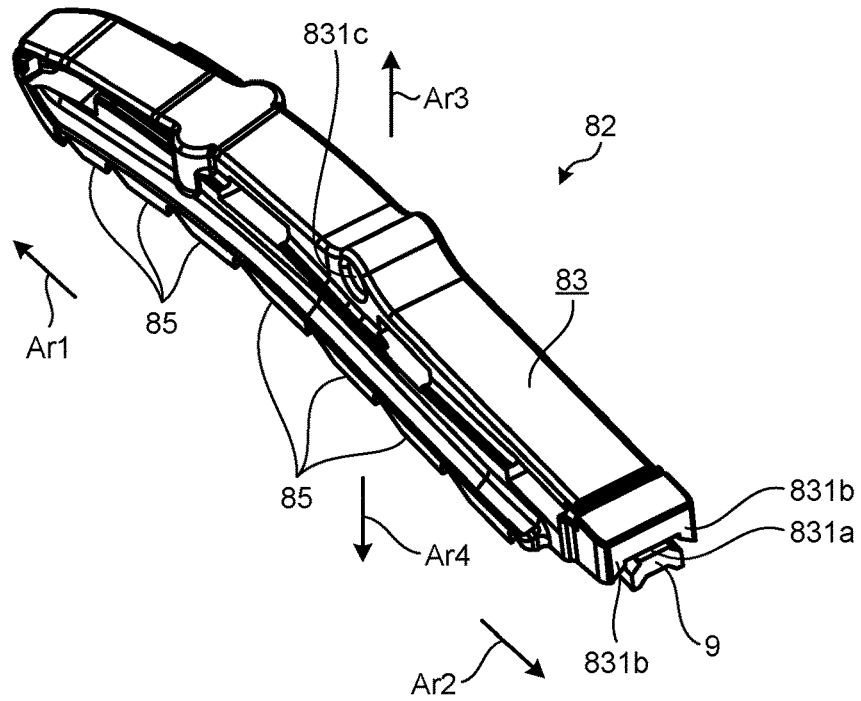
FIG. 7 is a view illustrating a wiper jaw.
Figure 8:
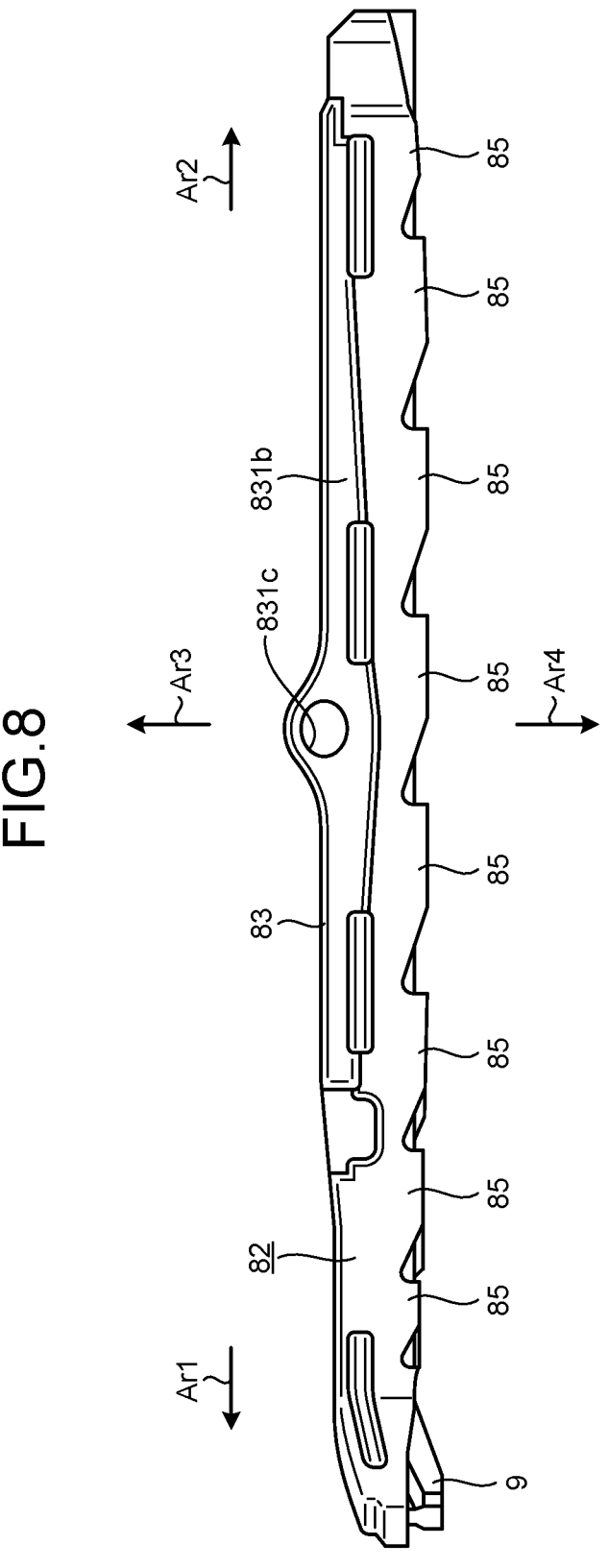
FIG. 8 is a view illustrating the wiper jaw.

FIGS. 7 and 8 are views illustrating the wiper jaw 82. Specifically, FIG. 7 is a perspective view of the wiper jaw 82 as viewed from the back surface side Ar3. FIG. 8 is a view of the wiper jaw 82 as viewed along the width direction. FIGS. 7 and 8 illustrate a state in which the resin pad 9 is assembled to the wiper jaw 82.

The wiper jaw 82 is made of an electrically conductive material such as stainless steel or a titanium alloy, and is attached to the arm 81. As illustrated in FIG. 7 or 8, the wiper jaw 82 includes a wiper jaw body 83, a plurality of first tooth portions 84 (FIG. 3), and a plurality of second tooth portions 85.

The wiper jaw body 83 is formed of an elongated plate body extending along the longitudinal direction of the arm body 811. In addition, an outer shape of the wiper jaw body 83 is set to be substantially the same as an inner surface shape of the first recess 811a. Then, the wiper jaw body 83 is disposed in the first recess 811a.

In the wiper jaw body 83, a second recess 831 (see FIG. 9) that penetrates from the proximal end to the distal end along the longitudinal direction of the wiper jaw body 83 and in which the resin pad 9 is disposed is provided on the surface on the treatment portion side Ar4. Hereinafter, a bottom surface of the second recess 831 is referred to as a bottom surface 831a, and side wall portions on both sides of the second recess 831 in the width direction are referred to as side wall portions 831b.

In addition, as illustrated in FIG. 7 or 8, the wiper jaw body 83 is provided with a fifth insertion hole 831c which penetrates from one side wall portion 831b to the other side wall portion 831b along the width direction and through which the first pin Pit is inserted. The fifth insertion hole 831c is positioned substantially at the center of the wiper jaw body 83 in the longitudinal direction. In addition, a central axis of the fifth insertion hole 831c is parallel to the width direction. Then, the wiper jaw body 83 is pivotally supported with respect to the arm 81 so as to be swingable about the first pin Pit. That is, by making the wiper jaw 82 swingable about the first pin Pit, a position where a strongest force is applied to the target site when the target site is gripped between the jaw 8 and the treatment portion 101 is positioned at substantially the center of the jaw 8 in the longitudinal direction instead of the proximal end side Ar2 of the jaw 8. As a result, a force is substantially uniformly applied to the target site gripped between the jaw 8 and the treatment portion 101.

The plurality of first tooth portions 84 protrude from the one side wall portion 831b toward the treatment portion side Ar4 respectively, and are arranged side by side along the longitudinal direction of the wiper jaw body 83.

The plurality of second tooth portions 85 protrude from the other side wall portion 831b toward the treatment portion side Ar4 respectively, and are arranged side by side along the longitudinal direction of the wiper jaw body 83.

Figure 9:
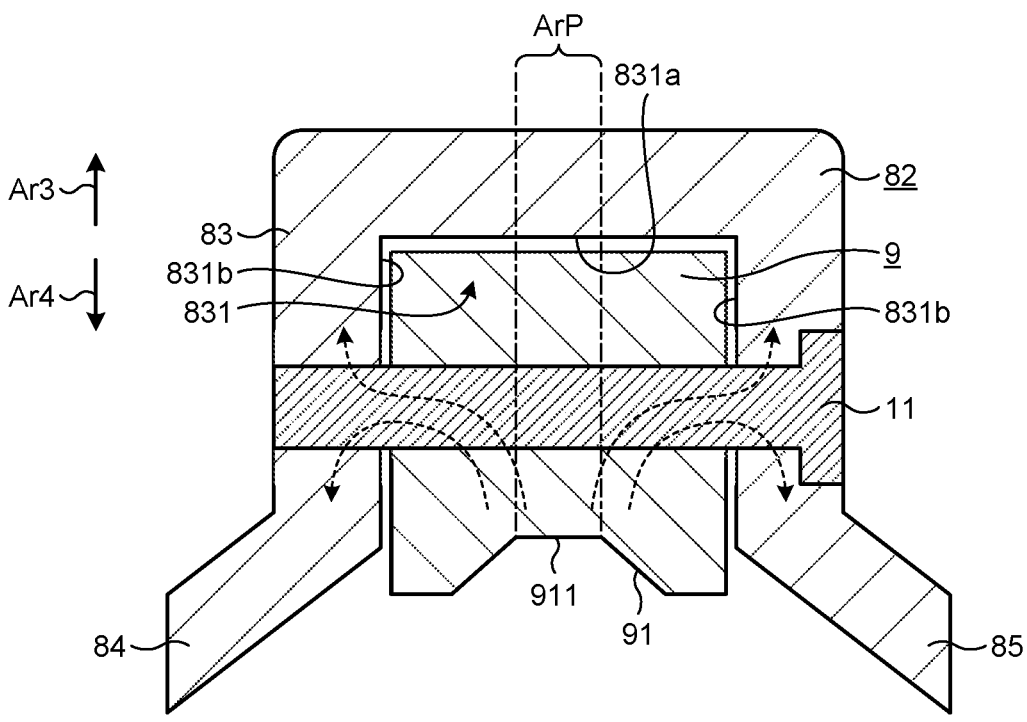
FIG. 9 is a view illustrating an attachment structure of a resin pad to the wiper jaw.

Then, the plurality of first tooth portions 84 and the plurality of second tooth portions 85 are provided in a state where the resin pad 9 is sandwiched in a state where the resin pad 9 is attached to the wiper jaw 82 (see FIG. 9).

The resin pad 9 is softer than the vibration transmitter 10, is made of a resin material having electrical insulation and biocompatibility, for example, polytetrafluoroethylene (PTFE), and has a substantially rectangular parallelepiped shape extending along the longitudinal direction of the arm body 811. In addition, in the resin pad 9, a third recess 91 (see FIG. 9) extending from the proximal end toward the distal end side Ar1 is provided on the surface on the treatment portion side Ar4. Further, the resin pad 9 is disposed inside the second recess 831. Then, when the jaw 8 is brought close to the treatment portion 101, a bottom surface 911 (see FIG. 9) of the third recess 91 of the resin pad 9 abuts on the treatment portion 101. The bottom surface 911 has a substantially flat shape. Then, the bottom surface 911 corresponds to a gripping surface. Hereinafter, for convenience of description, the bottom surface 911 is referred to as a gripping surface 911.

The attachment structure of the resin pad 9 to the jaw 8 will be described later in "Attachment Structure of Resin Pad to Jaw".

The vibration transmitter 10 has an elongated shape and is made of an electrically conductive material. Then, as illustrated in FIG. 2 or 3, the vibration transmitter 10 is inserted into the sheath 7 in a state where the treatment portion 101 is exposed to the outside. The vibration transmitter 10 includes the treatment portion 101 and a shaft 102.

The treatment portion 101 is provided at the distal end of the shaft 102. Similarly to the jaw 8, the treatment portion 101 extends along a curve toward the left side as it goes toward the distal end side Ar1 as viewed from the proximal end side Ar2 in a state where the jaw 8 is positioned on the upper side.

The shaft 102 has an elongated shape extending along the central axis Ax, and an end portion on the proximal end side Ar2 is coupled to a bolted Langevin type transducer (BLT) constituting the ultrasonic transducer 3. Then, the shaft 102 transfers the ultrasonic vibration generated by the BLT from the end portion on the proximal end side Ar2 to the treatment portion 101. In the present first embodiment, the ultrasonic vibration is longitudinal vibration that vibrates in a direction along the central axis Ax. At this time, the treatment portion 101 vibrates with a desired amplitude by the longitudinal vibration of the vibration transmitter 10.

An annular lining LI (see FIGS. 35 and 36) having electrical insulation and elasticity and extending along a circumferential direction around a central axis of the shaft 102 is attached to the outer peripheral surface of the shaft 102 described above. The lining LI is disposed at each position of a node of the longitudinal vibration of the vibration transmitter 10. Then, the lining LI abuts on the inner tube TI in a state where the vibration transmitter 10 is inserted into the sheath 7. The inner tube TI has a function of securing electrical insulation between the sheath 7 and the vibration transmitter 10. In addition, the lining LI has a function of sealing liquid that has entered a gap between the inner tube TI and the vibration transmitter 10.

The ultrasonic transducer 3 is detachably coupled to an end portion of the holding case 4 on the proximal end side Ar2. Although not specifically illustrated, the ultrasonic transducer 3 includes a BLT that generates ultrasonic vibration in response to supply of AC power.

The control device (not illustrated) electrically coupled to the ultrasonic treatment instrument 1 described above controls the operation of the ultrasonic treatment instrument 1 as described below according to the operation signal from the switch 6.

The control device supplies high-frequency power between the jaw 8 and the treatment portion 101 via the sheath 7 and the shaft 102. Then, a high-frequency current flows between the treatment portion 101 and the plurality of first and second tooth portions 84 and 85 having the same potential. That is, the high-frequency current flows through the target site gripped between the jaw 8 and the treatment portion 101. In other words, high-frequency energy is applied to the target site.

In addition, the control device supplies AC power to the BLT constituting the ultrasonic transducer 3 to generate ultrasonic vibration in the BLT. Then, ultrasonic vibration is applied from the treatment portion 101 to the target site gripped between the jaw 8 and the treatment portion 101. In other words, ultrasonic energy is applied to the target site.

Then, Joule heat is generated in the target site by the flow of the high-frequency current. In addition, frictional heat is generated between the treatment portion 101 and the target site by the vertical vibration of the treatment portion 101. As a result, the target site is incised while coagulating.

Attachment Structure of Resin Pad to Jaw

Next, an attachment structure of the resin pad 9 to the jaw 8 will be described.

FIG. 9 is a view illustrating the attachment structure of the resin pad 9 to the jaw 8. Specifically, FIG. 9 is a cross-sectional view of the wiper jaw 82 on which the resin pad 9 is taken, taken along a plane orthogonal to the longitudinal direction of the wiper jaw 82.

As illustrated in FIG. 9, the resin pad 9 is attached to the wiper jaw 82 by a heat transmitter 11 inside the second recess 831.

The heat transmitter 11 is configured separately from the jaw 8, and is a member that transfers the heat of the resin pad 9 from the resin pad 9 to the jaw 8 (wiper jaw 82). In the present first embodiment, the heat transmitter 11 is made of a material having higher thermal conductivity than the resin pad 9 and the wiper jaw 82. As a material of the heat transmitter 11, for example, aluminum, gold, silver, copper, or the like can be exemplified. In addition, the heat transmitter 11 may be made of the same material as the wiper jaw 82. In addition, as illustrated in FIG. 9, the heat transmitter 11 has a pin shape.

Then, in a state where the heat transmitter 11 penetrates the resin pad 9 in the width direction, end portions on one end side and the other end side are respectively coupled to the side wall portions 831b on both sides of the wiper jaw body 83 in the width direction. That is, the heat transmitter 11 is bridged between the wiper jaw body 83 and the resin pad 9. In this state, the substantially central portion of the heat transmitter 11 is positioned in a projection area ArP obtained by projecting the gripping surface 911 toward the back surface side Ar3 along the opening/closing direction of the jaw 8. Then, the heat of the gripping surface 911 moves along a heat transfer path of the resin pad 9 to the heat transmitter 11 to the wiper jaw body 83 to the first pin Pit and to the arm 81 as indicated by arrows in FIG. 9.

Although not specifically illustrated, a plurality of the heat transmitters 11 are arranged side by side at predetermined intervals along the longitudinal direction of the resin pad 9. That is, the resin pad 9 is attached to the wiper jaw body 83 by the plurality of heat transmitters 11 inside the second recess 831.

According to the present first embodiment described above, the following effects are obtained.

The ultrasonic treatment instrument 1 according to the present first embodiment includes the heat transmitter 11 that is configured separately from the jaw 8 and transfers the heat of the resin pad 9 from the resin pad 9 to the jaw 8 (wiper jaw 82).

Therefore, frictional heat generated in the resin pad 9 (gripping surface 911) by application of ultrasonic vibration can be moved along the heat transfer path of the resin pad 9 to a heat transmitter 11 and to the jaw 8.

Therefore, according to the ultrasonic treatment instrument 1 according to the present first embodiment, deterioration of the resin pad 9 can be suppressed.

In particular, the heat transmitter 11 is made of a material having higher thermal conductivity than the resin pad 9. Therefore, a dissipation efficiency of heat from the resin pad 9 along the heat transfer path described above can be improved, and the deterioration of the resin pad 9 can be further suppressed.

In addition, a portion of the heat transmitter 11 is positioned in the projection area ArP where frictional heat generated on the gripping surface 911 is easily transferred in the resin pad 9. Therefore, the heat of the resin pad 9 can be effectively received by the heat transmitter 11, and the heat can be dissipated along the heat transfer path described above, and the deterioration of the resin pad 9 can be further suppressed.

Second Embodiment

Next, the present second embodiment will be described.

In the following description, the same reference numerals are given to the same configurations as those of the above-described first embodiment, and a detailed description thereof will be omitted or simplified.

The present second embodiment is different from the above-described first embodiment in the attachment structure of the resin pad 9 to the jaw 8. Hereinafter, for convenience of description, the jaw 8 and the wiper jaw 82 according to the present second embodiment are referred to as a jaw 8A and a wiper jaw 82A, respectively. In addition, the resin pad 9 according to the present second embodiment is referred to as a resin pad 9A.

Figure 10:
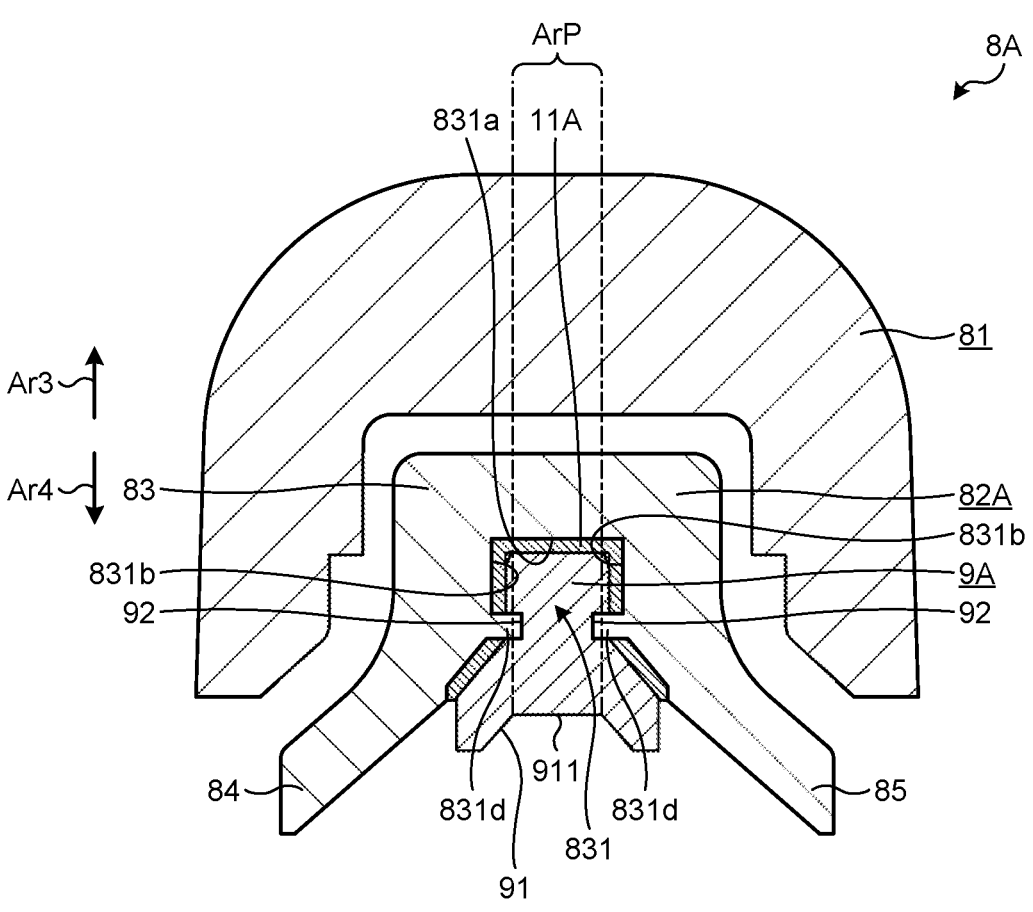
FIG. 10 is a view illustrating an attachment structure of a resin pad to a jaw according to a second embodiment.

FIG. 10 is a view illustrating an attachment structure of the resin pad 9A to the jaw 8A according to the second embodiment. Specifically, FIG. 9 is a cross-sectional view of the resin pad 9A and the jaw 8A taken along a plane orthogonal to the longitudinal direction of the jaw 8A. In FIG. 10, for convenience of explanation, the arm 81 and the resin cover RC in the jaw 8A are illustrated as one member.

The jaw 8A is different from the jaw 8 described in the above-described first embodiment in that a wiper jaw 82A having a different shape from the wiper jaw 82 is adopted.

As illustrated in FIG. 10, the wiper jaw 82A is different from the wiper jaw 82 described in the above-described first embodiment in that a pair of claws 831*d* are provided.

As illustrated in FIG. 10, the pair of claws 831*d* linearly protrude in directions approaching each other from positions facing each other along the width direction in each side wall portion 831*b*, and extend along the longitudinal direction of the wiper jaw 82A.

In addition, as illustrated in FIG. 10, the resin pad 9A is different from the resin pad 9 described in the above-described first embodiment in that a pair of slits 92 are provided.

As illustrated in FIG. 10, in the resin pad 9A, the pair of slits 92 are provided on each side surface intersecting the surface on the treatment portion side Ar4 in a state of penetrating from the distal end toward the proximal end along the longitudinal direction of the resin pad 9A. Then, the resin pad 9A is attached to the wiper jaw 82A by being slid along the longitudinal direction of the wiper jaw 82A in a state where the pair of claws 831*d* enter the pair of slits 92 inside the second recess 831. That is, in the present second embodiment, the heat transmitter 11 described in the above-described first embodiment is omitted.

The installation method of the resin pad 9A is not limited to the sliding method described above. For example, by using the elasticity of the resin pad 9A, an installation method in which the resin pad 9A is screwed until the pair of claws 831*d* enter the pair of slits 92 from the lower side to the upper side in FIGS. 10 and 11 may be adopted.

In the present second embodiment, as illustrated in FIG. 10, a heat transmitter 11A is disposed between an outer surface of the resin pad 9A and the bottom surface 831*a*, the side wall portions 831*b*, and the first and second tooth portions 84 and 85 in a state of avoiding the pair of claws 831*d*. In this state, in the heat transmitter 11A, a central portion in the width direction of a portion disposed between the outer surface of the resin pad 9A and the bottom surface 831*a* is positioned in the projection area ArP as illustrated in FIG. 10.

Similarly to the heat transmitter 11 described in the above-described first embodiment, the heat transmitter 11A is a member that is configured separately from the jaw 8A and transfers the heat of the resin pad 9A from the resin pad 9A to the jaw 8A (wiper jaw 82A). In the present second embodiment, the heat transmitter 11A has a sheet shape and is made of a material having higher thermal conductivity than the resin pad 9A. For example, the heat transmitter 11A is a graphite sheet. Then, the heat of the gripping surface 911 moves along a heat transfer path of the resin pad 9A to the heat transmitter 11A to the wiper jaw 82A to the first pin Pit and to the arm 81.

The heat transmitter 11A may have the same length dimension as the entire length of the resin pad 9A in the longitudinal direction, or may have a length dimension shorter than the entire length.

Even in the case of adopting the structure in the above-described present second embodiment, the same effects as those of the above-described first embodiment are obtained.

In the above-described first embodiment, the heat transmitter 11A may be disposed between the outer surface of the resin pad 9 and the bottom surface 831*a*, the side wall portions 831*b*, and the first and second tooth portions 84 and 85.

Modification 2-1 of Second Embodiment

Figure 11:
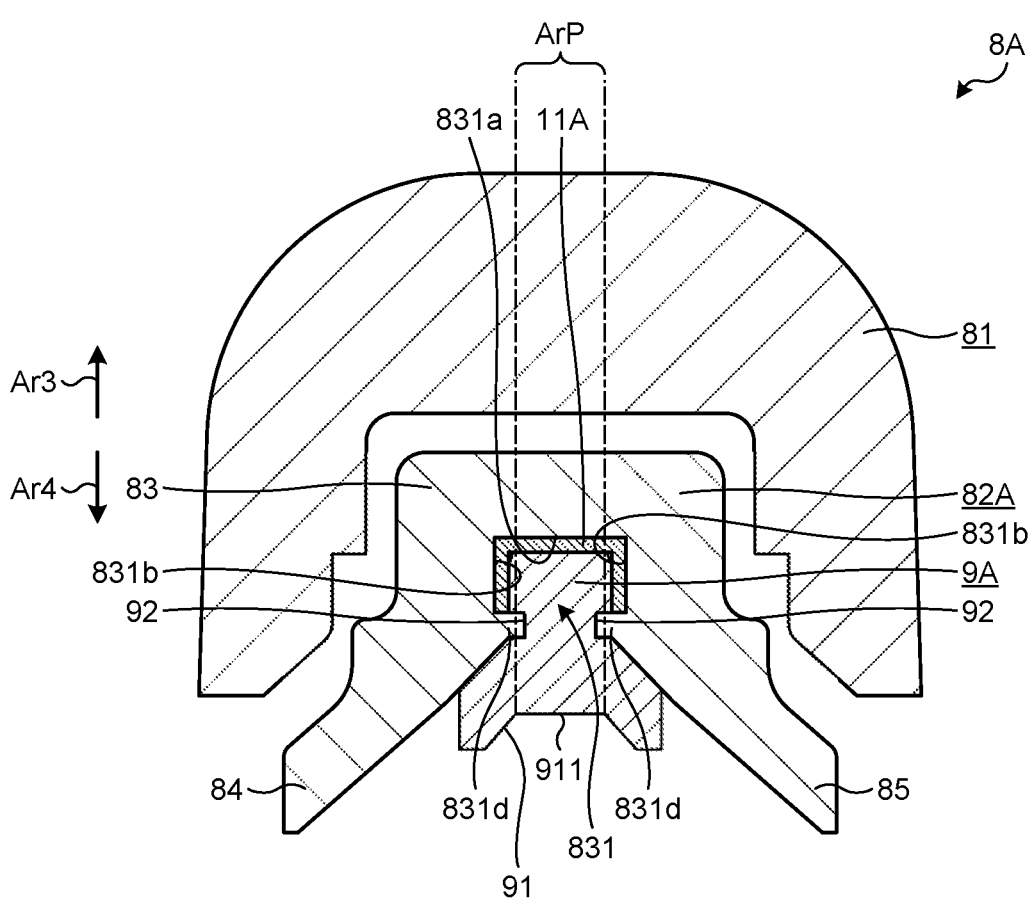
FIG. 11 is a view illustrating Modification 2-1 of the second embodiment.

FIG. 11 is a view illustrating Modification 2-1 of the second embodiment. Specifically, FIG. 11 is a cross-sectional view corresponding to FIG. 10.

In the above-described second embodiment, as in the present Modification 2-1 illustrated in FIG. 11, the heat transmitter 11A may be disposed only between the outer surface of the resin pad 9A and the bottom surface 831*a* and the side wall portions 831*b* in a state of avoiding the pair of claws 831*d*.

Third Embodiment

Next, the present third embodiment will be described.

In the following description, the same reference numerals are given to the same configurations as those of the above-described first embodiment, and a detailed description thereof will be omitted or simplified.

The present third embodiment is different from the above-described first embodiment in the attachment structure of the resin pad 9 to the jaw 8. Hereinafter, for convenience of description, the jaw 8 and the wiper jaw 82 according to the present second embodiment are referred to as a jaw 8B and a wiper jaw 82B, respectively. In addition, the resin pad 9 according to the present second embodiment will be referred to as a resin pad 9B.

Figure 12:
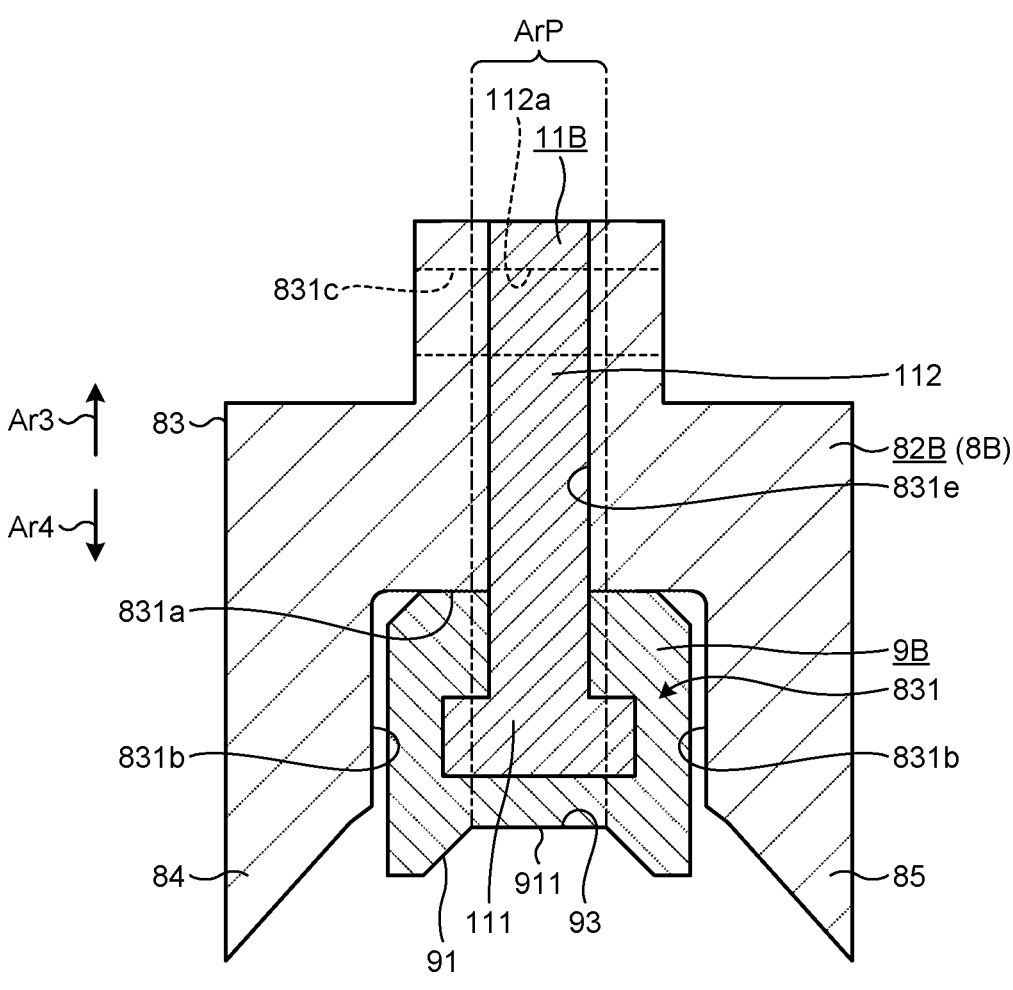
FIG. 12 is a view illustrating an attachment structure of a resin pad to a jaw according to a third embodiment.

FIG. 12 is a view illustrating an attachment structure of the resin pad 9B to the jaw 8B. Specifically, FIG. 12 is a cross-sectional view corresponding to FIG. 9.

The jaw 8B is different from the jaw 8 described in the above-described first embodiment in that the wiper jaw 82B having a different shape from the wiper jaw 82 is adopted.

As illustrated in FIG. 12, the wiper jaw 82B is different from the wiper jaw 82 described in the above-described first embodiment in that a sixth insertion hole 831*e* is provided.

The sixth insertion hole 831*e* is positioned substantially at the center of the wiper jaw body 83 in the longitudinal direction, and penetrates from the upper outer surface to the inside of the second recess 831 through the fifth insertion hole 831*c* in FIG. 12.

In addition, as illustrated in FIG. 12, the resin pad 9B is different from the resin pad 9 described in the above-described first embodiment in that a groove portion 93 is provided.

The groove portion 93 corresponds to an engagement receiving portion. The groove portion 93 linearly extends from the surface facing the bottom surface 831*a* toward the gripping surface 911 in the resin pad 9B, and has a T-shaped cross section in which the extended distal end portions linearly extend in the width direction, respectively. Then, the groove portion 93 penetrates from the distal end to the proximal end of the resin pad 9B along the longitudinal direction of the resin pad 9B.

Then, as illustrated in FIG. 12, the resin pad 9B is attached to the wiper jaw 82B by a heat transmitter 11B different from the heat transmitter 11 described in the first embodiment inside the second recess 831.

Figure 13:
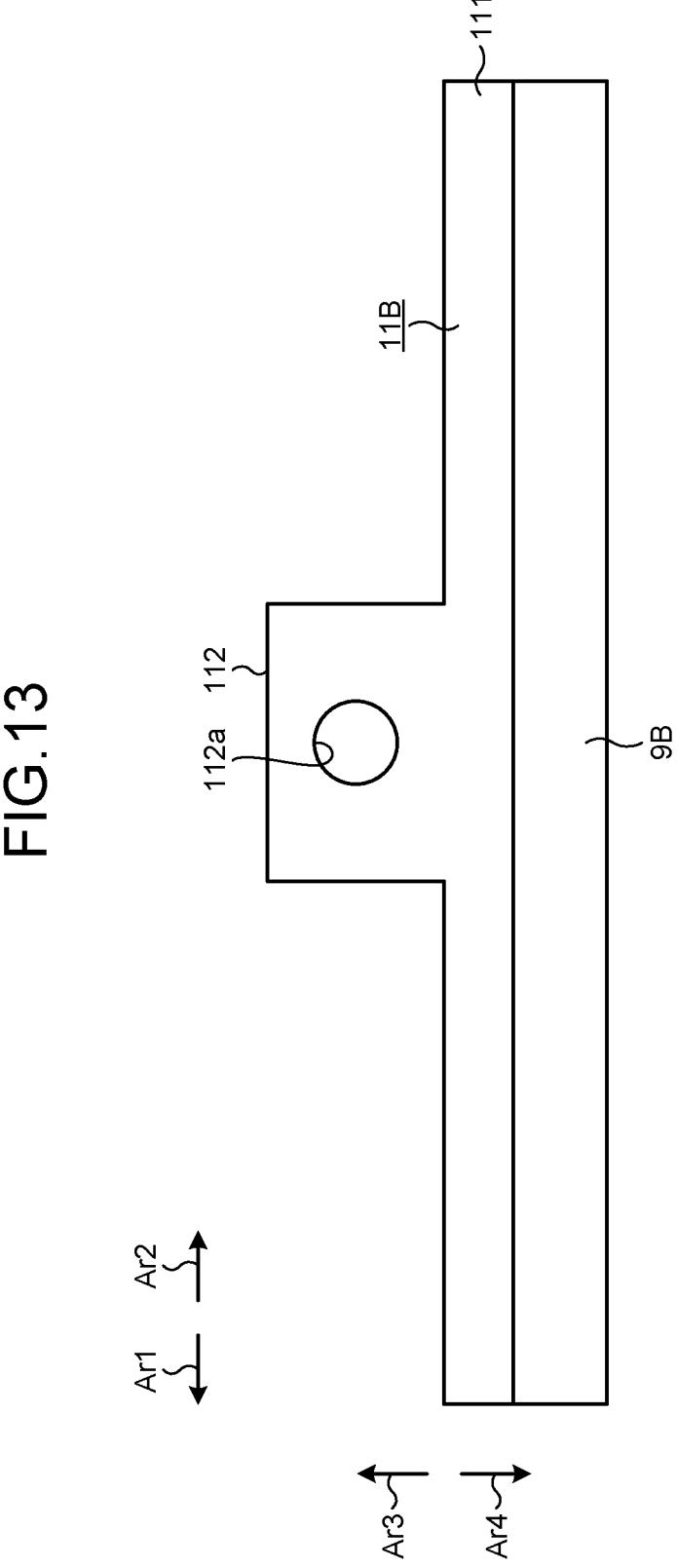
FIG. 13 is a view illustrating a heat transmitter.

FIG. 13 is a view illustrating the heat transmitter 11B. Specifically, FIG. 13 is a view of the heat transmitter 11B to which the resin pad 9B is attached as viewed along the width direction.

Similarly to the heat transmitter 11 described in the above-described first embodiment, the heat transmitter 11B is a member that is configured separately from the jaw 8B and transfers the heat of the resin pad 9B from the resin pad 9B to the jaw 8B (wiper jaw 82B). In the present third embodiment, the heat transmitter 11B is made of a material having higher thermal conductivity than the resin pad 9B and the wiper jaw 82B. As a material of the heat transmitter 11B, for example, aluminum, gold, silver, copper, or the like can be exemplified. In addition, the heat transmitter 11B may be made of the same material as the wiper jaw 82B. Then, as illustrated in FIG. 12 or 13, the heat transmitter 11B includes a pad side coupling portion 111 and a jaw side coupling portion 112.

The pad side coupling portion 111 is a portion coupled to the resin pad 9B and corresponds to an engaging portion. The pad side coupling portion 111 is formed in an elongated shape having a length dimension substantially the same as the entire length of the resin pad 9B in the longitudinal direction, and has a T-shaped cross section substantially the same as the groove portion 93. Then, as illustrated in FIG. 12, the pad side coupling portion 111 is inserted (engaged) into groove portion 93. As a result, the heat transmitter 11B holds the resin pad 9B. In this state, most of the heat transmitter 11B is positioned in the projection area ArP.

The jaw side coupling portion 112 is a portion coupled to the jaw 8B and corresponds to a coupling portion. The jaw side coupling portion 112 protrudes upward in FIG. 12 from a substantially central portion of the pad side coupling portion 111 in the longitudinal direction at an upper end portion of the pad side coupling portion 111 in FIG. 12. In addition, as illustrated in FIG. 12 or 13, the jaw side coupling portion 112 is provided with a seventh insertion hole 112a penetrating along the width direction.

In the heat transmitter 11B described above, the first pin Pit is inserted into the seventh insertion hole 112a together with the fifth insertion hole 831c in a state where the jaw side coupling portion 112 is inserted into the sixth insertion hole 831e. As a result, the heat transmitter 11B and the resin pad 9B are pivotally supported with respect to the arm 81 so as to be swingable about the first pin Pit together with the wiper jaw 82B.

Then, the heat of the gripping surface 911 moves along a heat transfer path of the resin pad 9B to the heat transmitter 11B to the wiper jaw 82B and to the arm 81.

The coupling between the heat transmitter 11B and the jaw 8B is not limited to the above-described structure, and other mechanical coupling structures may be adopted, or a thermally conductive adhesive may be used.

Even in the case of adopting the structure in the above-described present third embodiment, the same effects as those of the above-described first embodiment are obtained.

Fourth Embodiment

Next, the present fourth embodiment will be described. In the following description, the same reference numerals are given to the same configurations as those of the above-described first embodiment, and a detailed description thereof will be omitted or simplified.

The present fourth embodiment is different from the above-described first embodiment in the attachment structure of the resin pad 9 to the jaw 8. Hereinafter, for convenience of description, the jaw 8 and the wiper jaw 82 according to the present fourth embodiment are referred to as a jaw 8C and a wiper jaw 82C, respectively. In addition, the resin pad 9 according to the present fourth embodiment is referred to as a resin pad 9C.

Figure 14:
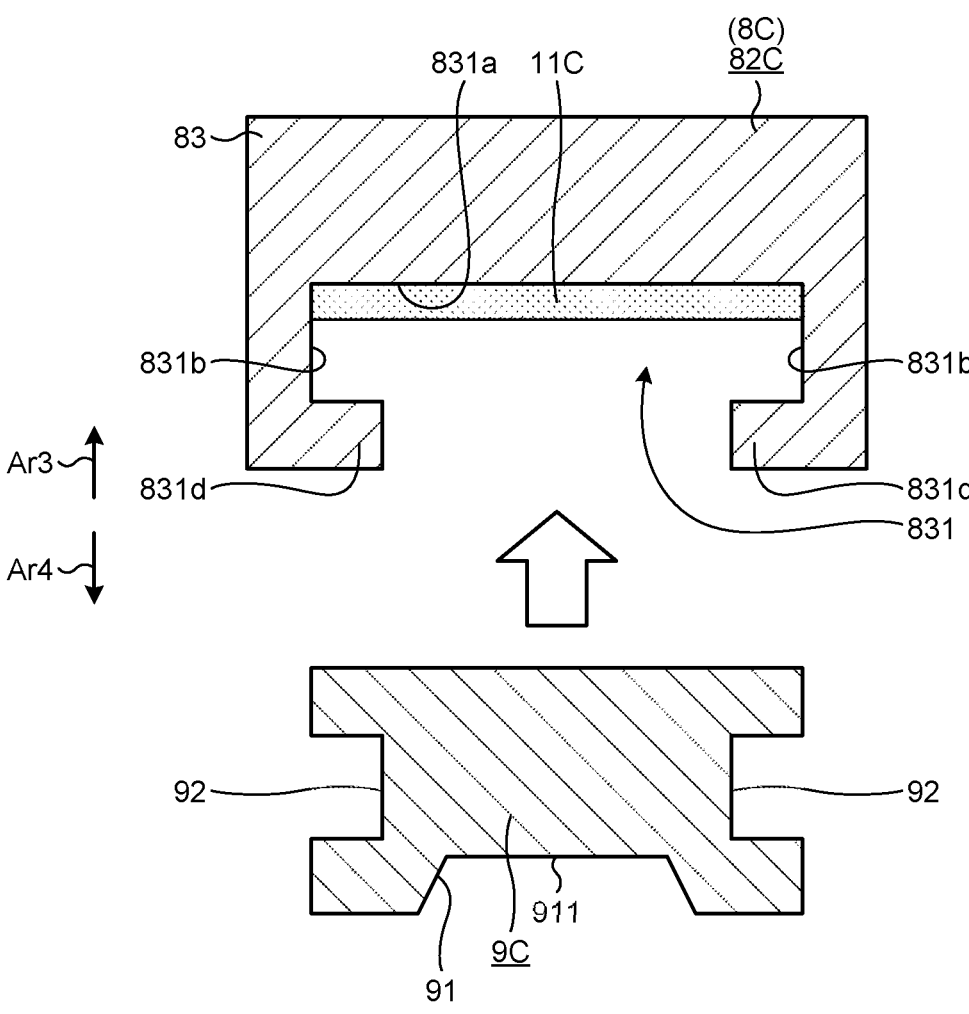
FIG. 14 is a view illustrating an attachment structure of a resin pad to a jaw according to a fourth embodiment.
Figure 15:
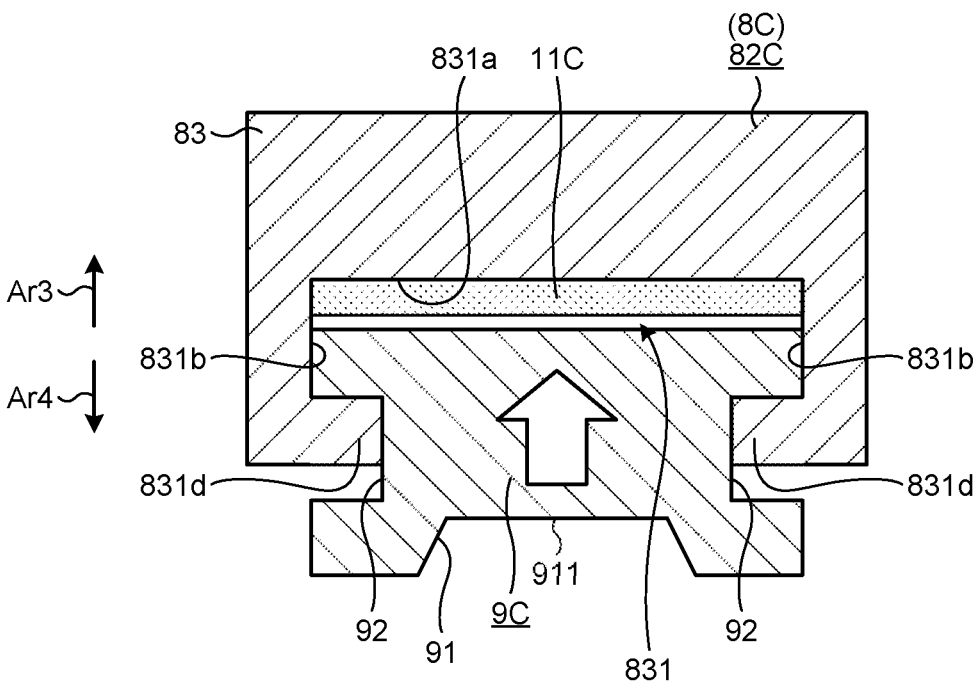
FIG. 15 is a view illustrating the attachment structure of the resin pad to the jaw according to the fourth embodiment.
Figure 16:
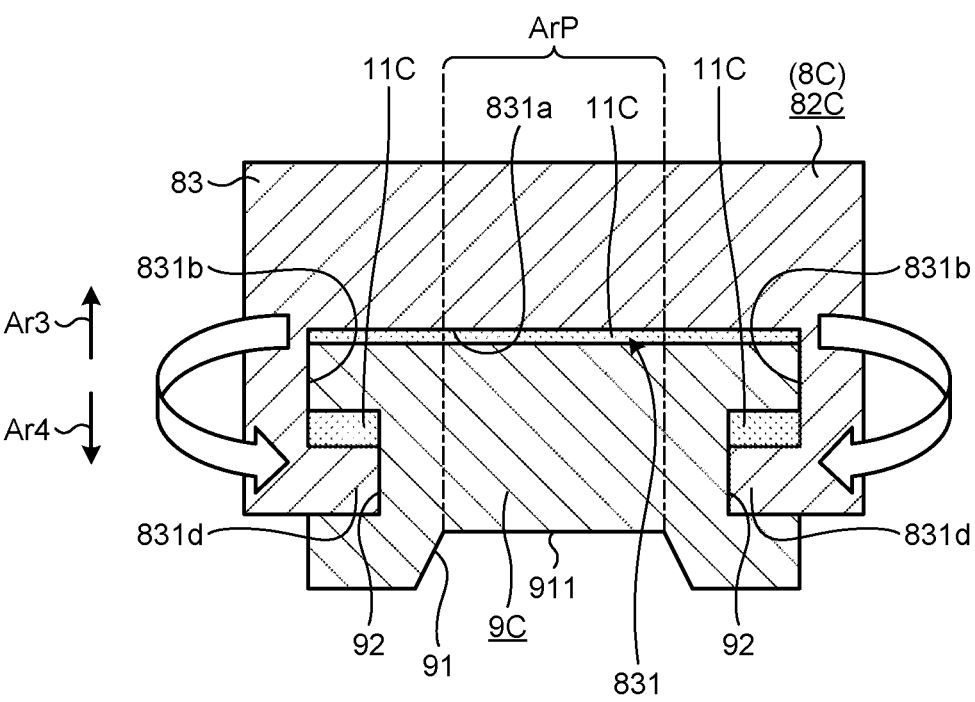
FIG. 16 is a view illustrating the attachment structure of the resin pad to the jaw according to the fourth embodiment.

FIGS. 14 to 16 are views illustrating an attachment structure of the resin pad 9C to the jaw 8C according to the fourth embodiment. Specifically, FIGS. 14 to 16 are cross-sectional views corresponding to FIG. 9, and sequentially illustrate an installation method of a heat transmitter 11C and the resin pad 9C with respect to the wiper jaw 82C. In FIGS. 14 to 16, illustration of the first and second tooth portions 84 and 85 is omitted for convenience of description.

The jaw 8C is different from the jaw 8 described in the above-described first embodiment in that the wiper jaw 82C having a different shape from the wiper jaw 82 is adopted.

As illustrated in FIGS. 14 to 16, the wiper jaw 82C is similar to the wiper jaw 82A described in the above-described second embodiment.

In addition, as illustrated in FIGS. 14 to 16, the resin pad 9C is similar to the resin pad 9A described in the above-described second embodiment. That is, similarly to the resin pad 9A described in the above-described second embodiment, the resin pad 9C is attached to the wiper jaw 82C in a state where the pair of claws 831d enter the pair of slits 92 inside the second recess 831. Therefore, in the present fourth embodiment, the heat transmitter 11 described in the above-described first embodiment is omitted.

The installation method of the resin pad 9C is not limited to the sliding method described above. For example, by using the elasticity of the resin pad 9C, an installation method in which the resin pad 9C is screwed until the pair of claws 831d enter the pair of slits 92 in the direction indicated by an arrow in FIG. 14 may be adopted.

In the present fourth embodiment, as illustrated in FIGS. 14 to 16, the heat transmitter 11C is disposed between an outer surface of the resin pad 9C and an inner surface of the second recess 831 inside the second recess 831.

Similarly to the heat transmitter 11 described in the above-described first embodiment, the heat transmitter 11C is a member that is configured separately from the jaw 8C and transfers the heat of the resin pad 9C from the resin pad 9C to the jaw 8C (wiper jaw 82C). In the present third embodiment, the heat transmitter 11C is an adhesive including a thermal conductive substance or a heat sealing sheet. As the thermal conductive substance, boron nitride, alumina, metal powder, carbon nanotube, silicon carbide, and the like can be exemplified.

Then, for example, as described below, the heat transmitter 11C is provided between the outer surface of the resin pad 9C and the inner surface of the second recess 831 inside the second recess 831.

First, as illustrated in FIG. 14, the worker applies or disposes the heat transmitter 11C on the bottom surface 831a. Next, as illustrated in FIG. 15, the worker sets a state in which the pair of claws 831d enter the pair of slits 92. Then, the worker presses the resin pad 9C toward the bottom surface 831a as indicated by an arrow in FIG. 15. As a result, as illustrated in FIG. 16, a portion of the heat transmitter 11C enters between the claw 831d and the slit 92 from between the resin pad 9C and the bottom surface 831a. In this state, in the heat transmitter 11C, the central portion of the portion disposed between the outer surface of the resin pad 9C and the bottom surface 831*a* in the width direction is positioned in the projection area ArP.

Then, the heat of the gripping surface 911 moves along a heat transfer path of the resin pad 9C to the heat transmitter 11C to the wiper jaw 82C to the first pin Pit and to the arm 81.

The heat transmitter 11C may have the same length dimension as the entire length of the resin pad 9C in the longitudinal direction, or may have a length dimension shorter than the entire length.

Even in the case of adopting the structure in the present fourth embodiment described above, the same effects as those of the above-described first embodiment are obtained.

In addition, the heat transmitter 11C is an adhesive including a thermal conductive substance or a heat sealing sheet. Therefore, a cross-sectional area of the heat transfer path of the resin pad 9C to the wiper jaw 82C can be enlarged, and a thermal resistance in the heat transfer path can be reduced.

Modification 4-1 of Fourth Embodiment

Figure 17:
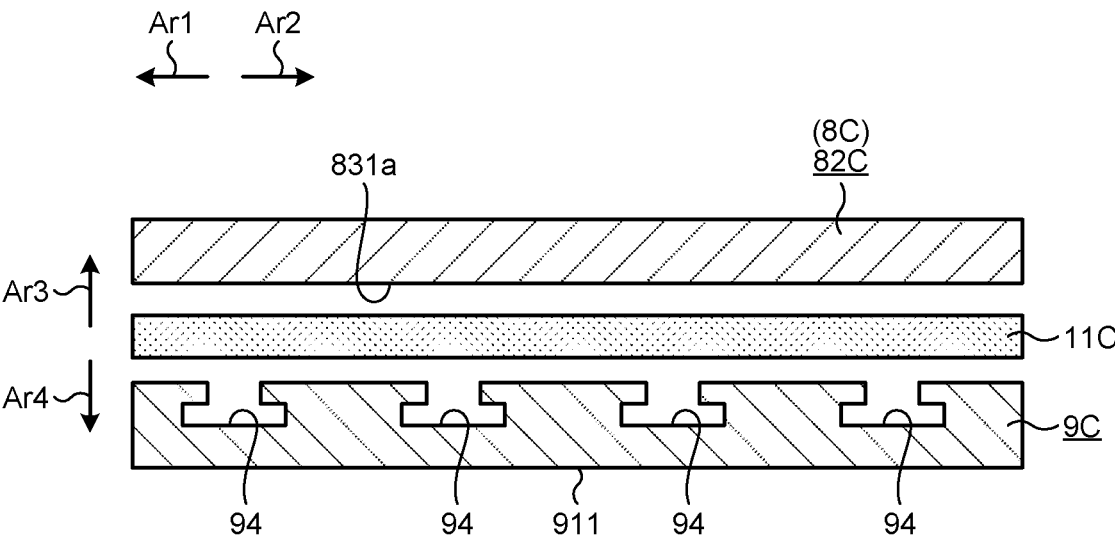
FIG. 17 is a view illustrating Modification 4-1 of the fourth embodiment.
Figure 18:
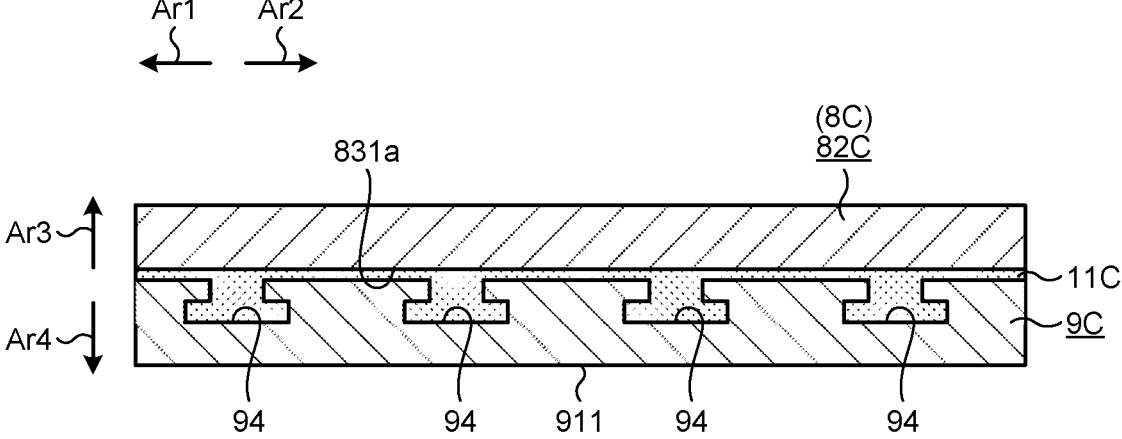
FIG. 18 is a view illustrating Modification 4-1 of the fourth embodiment.

FIGS. 17 and 18 are views illustrating Modification 4-1 of the fourth embodiment. Specifically, FIGS. 17 and 18 are cross-sectional views of the wiper jaw 82C, the resin pad 9C, and the heat transmitter 11C according to the present Modification 4-1 as viewed along the width direction, and sequentially illustrate the installation method of the resin pad 9C and the heat transmitter 11C with respect to the wiper jaw 82C.

In the above-described fourth embodiment, a plurality of coupling holes 94 may be provided on the surface of the resin pad 9C facing the bottom surface 831*a* as in the present Modification 4-1 illustrated in FIGS. 17 and 18.

As illustrated in FIG. 17 or 18, the coupling hole 94 extends linearly from the surface of the resin pad 9C facing the bottom surface 831*a* toward the gripping surface 911, and has a cross-sectional T shape in which the extended distal end portions extend linearly in the longitudinal direction of the resin pad 9C respectively. Then, the plurality of coupling holes 94 are arranged side by side along the longitudinal direction of the resin pad 9C.

Then, as described in the above-described fourth embodiment, after the heat transmitter 11C is applied or disposed on the bottom surface 831*a* and the pair of claws 831*d* enter the pair of slits 92, the resin pad 9C is pressed toward the bottom surface 831*a*. As a result, as illustrated in FIG. 18, a portion of the heat transmitter 11C enters the plurality of coupling holes 94 from between the resin pad 9C and the bottom surface 831*a*.

Therefore, a bonding strength of the resin pad 9C to the wiper jaw 82C is improved, the cross-sectional area of the heat transfer path of the resin pad 9C to the wiper jaw 82C is enlarged, and the thermal resistance in the heat transfer path can be reduced.

Fifth Embodiment

Next, the present fifth embodiment will be described.

In the following description, the same reference numerals are given to the same configurations as those of the above-described first embodiment, and a detailed description thereof will be omitted or simplified.

The present fifth embodiment is different from the above-described first embodiment in the attachment structure of the resin pad 9 to the jaw 8. Hereinafter, for convenience of description, the jaw 8 and the wiper jaw 82 according to the present fifth embodiment are referred to as a jaw 8D and a wiper jaw 82D, respectively. In addition, the resin pad 9 according to the present fifth embodiment will be referred to as a resin pad 9D.

Figure 19:
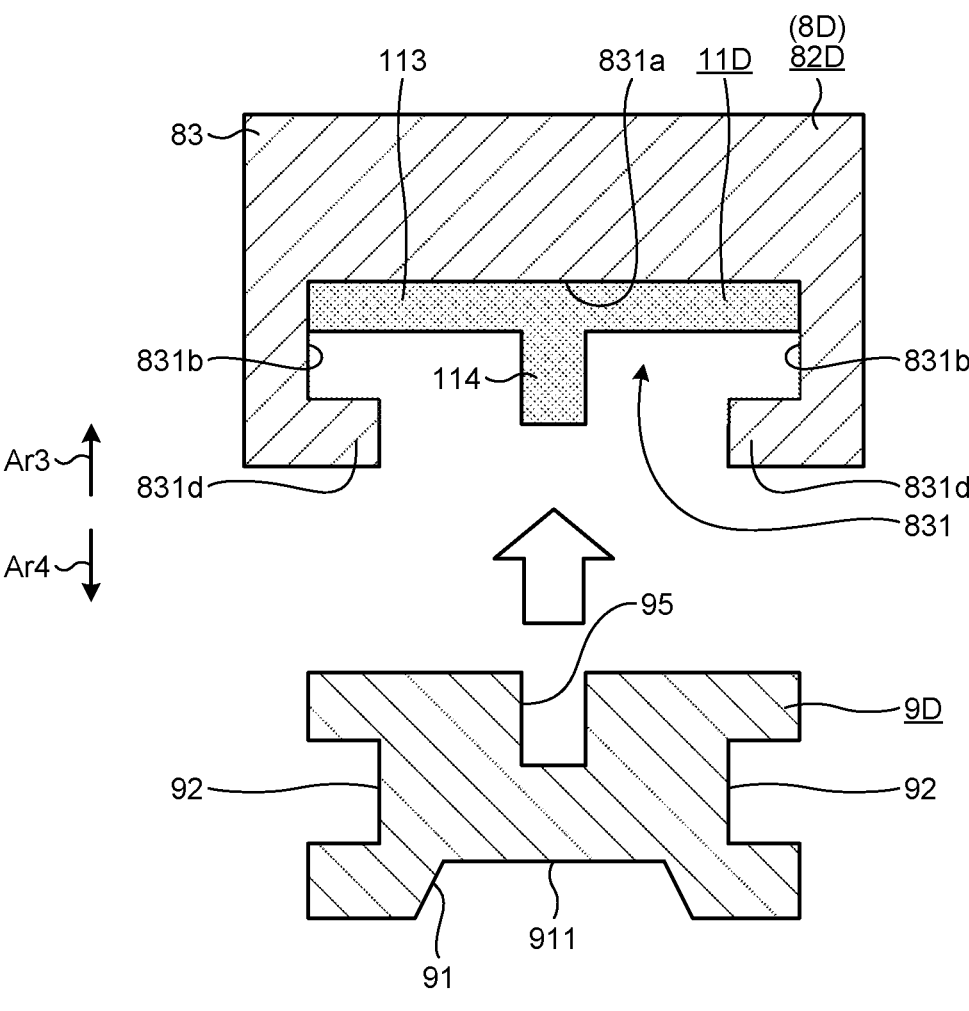
FIG. 19 is a view illustrating an attachment structure of a resin pad to a jaw according to a fifth embodiment.
Figure 20:
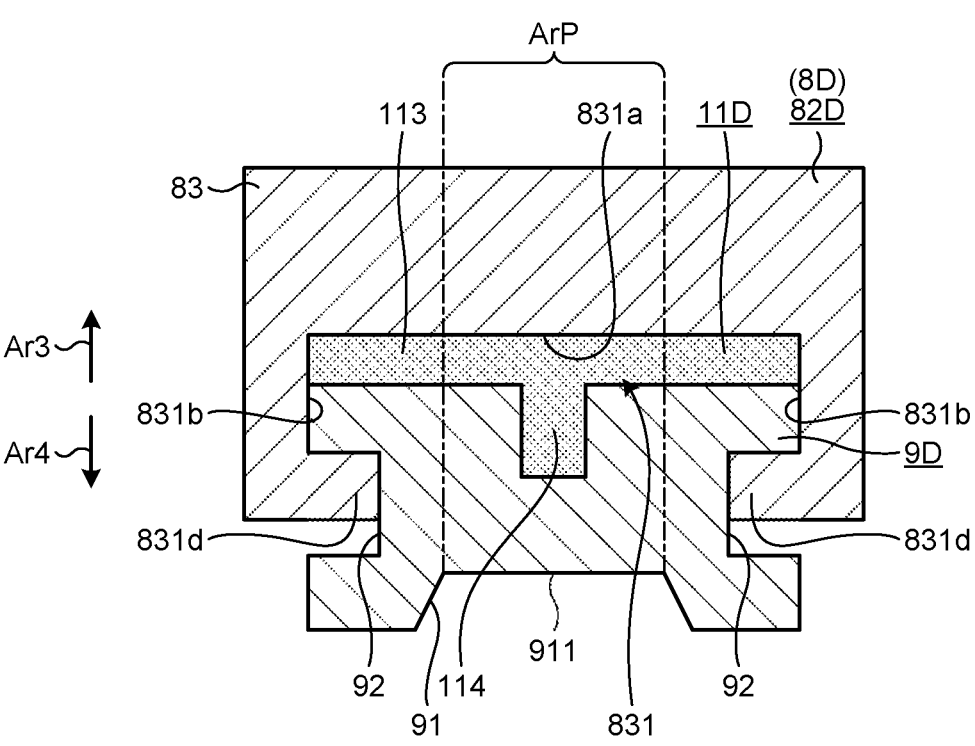
FIG. 20 is a view illustrating the attachment structure of the resin pad to the jaw according to the fifth embodiment.

FIGS. 19 and 20 are views illustrating an attachment structure of the resin pad 9D to the jaw 8D according to the fifth embodiment. Specifically, FIGS. 19 and 20 are cross-sectional views corresponding to FIG. 9, and sequentially illustrate an installation method of the resin pad 9D and a heat transmitter 11D with respect to the wiper jaw 82D. In FIGS. 19 and 20, illustration of the first and second tooth portions 84 and 85 is omitted for convenience of description.

The jaw 8D is different from the jaw 8 described in the above-described first embodiment in that the wiper jaw 82D having a different shape from the wiper jaw 82 is adopted.

As illustrated in FIG. 19 or 20, the wiper jaw 82D is similar to the wiper jaw 82A described in the above-described second embodiment.

As illustrated in FIG. 19 or 20, the resin pad 9D is different from the resin pad 9 described in the above-described first embodiment in that the pair of slits 92 and a groove portion 95 described in the above-described second embodiment are provided. That is, the resin pad 9D is attached to the wiper jaw 82D in a state where the pair of claws 831*d* enter the pair of slits 92 inside the second recess 831. Therefore, in the present fifth embodiment, the heat transmitter 11 described in the above-described first embodiment is omitted.

The groove portion 95 corresponds to a recess. As illustrated in FIG. 19 or 20, the groove portion 95 linearly extends from the surface of the resin pad 9D facing the bottom surface 831*a* toward the gripping surface 911, and penetrates from the distal end to the proximal end of the resin pad 9D along the longitudinal direction of the resin pad 9D.

In the present fifth embodiment, as illustrated in FIG. 19 or 20, the heat transmitter 11D is disposed between the bottom surface 831*a* and the resin pad 9D inside the second recess 831.

Similarly to the heat transmitter 11 described in the above-described first embodiment, the heat transmitter 11D is a member that is configured separately from the jaw 8D and transfers the heat of the resin pad 9D from the resin pad 9D to the jaw 8D (wiper jaw 82D). In the present fifth embodiment, the heat transmitter 11D is made of a material having higher thermal conductivity than the resin pad 9D and the wiper jaw 82D. As a material of the heat transmitter 11D, for example, aluminum, gold, silver, copper, graphite, or the like can be exemplified. In addition, the heat transmitter 11D may be made of the same material as the wiper jaw 82B. Then, as illustrated in FIG. 19 or 20, the heat transmitter 11D includes an abutment portion 113 and a protrusion 114.

The abutment portion 113 is formed of a plate body having a length dimension substantially equal to the length dimension of the bottom surface 831*a* in the width direction, and one plate surface abuts on the bottom surface 831*a*.

The protrusion 114 linearly protrudes from a substantially central position in the width direction toward the resin pad 9D on the other plate surface of the abutment portion 113 and is fitted into the groove portion 95.

The heat transmitter 11D may have the same length dimension as the entire length of the resin pad 9D in the longitudinal direction, or may have a length dimension shorter than the entire length.

Then, for example, as described below, the heat transmitter 11D is provided between an outer surface of the resin pad 9D and the bottom surface 831a inside the second recess 831.

First, as illustrated in FIG. 19, the worker disposes the heat transmitter 11D inside the second recess 831 in a state where the abutment portion 113 can abut on the bottom surface 831a. Then, the worker slides the resin pad 9D along the longitudinal direction of the wiper jaw 82D in a state where the pair of claws 831d enter the pair of slits 92 and the protrusion 114 enters the groove portion 95. As a result, as illustrated in FIG. 20, the resin pad 9C is installed inside the second recess 831 while being coupled to the resin pad 9D. In this state, the central portion of the heat transmitter 11D in the width direction is positioned in the projection area ArP.

The installation method of the resin pad 9D is not limited to the sliding method described above. For example, by using the elasticity of the resin pad 9D, an installation method in which the resin pad 9D is screwed until the pair of claws 831d enter the pair of slits 92 and the protrusion 114 enters the groove portion 95 in the direction indicated by an arrow in FIG. 19 may be adopted.

Then, the heat of the gripping surface 911 moves along a heat transfer path of the resin pad 9D to the heat transmitter 11D to the wiper jaw 82D to the first pin Pit and to the arm 81.

The coupling between the heat transmitter 11D and the resin pad 9D is not limited to the above-described structure, and other mechanical coupling structures may be adopted, or a thermally conductive adhesive may be used. In addition, the heat transmitter 11D and the wiper jaw 82D may be coupled by a thermally conductive adhesive.

Even in the case of adopting the structure in the present fifth embodiment described above, the same effects as those of the above-described first embodiment are obtained.

Modification 5-1 of Fifth Embodiment

Figure 21:
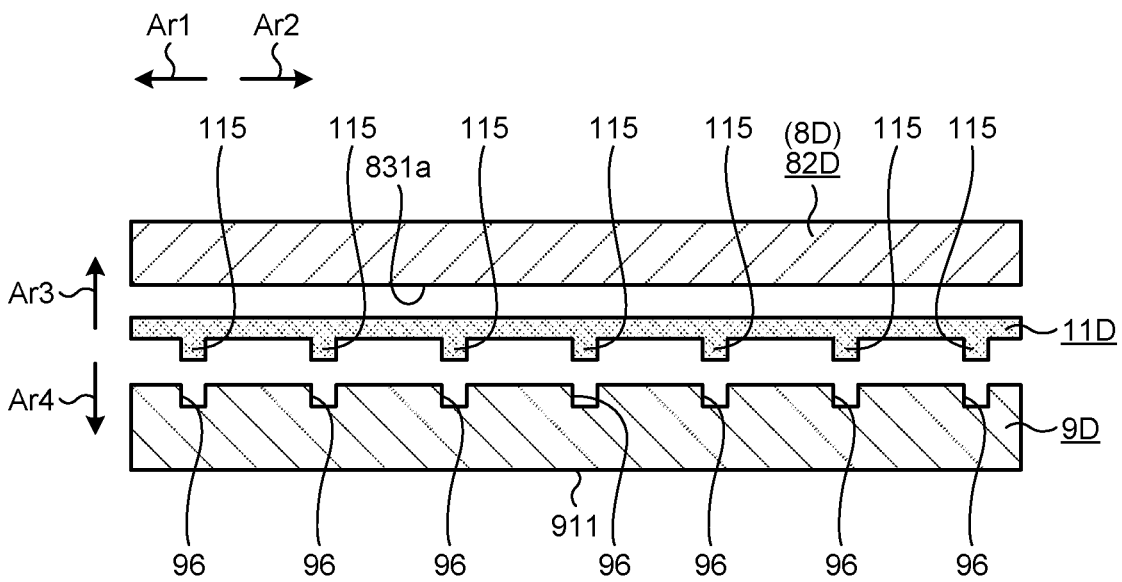
FIG. 21 is a view illustrating Modification 5-1 of the fifth embodiment.
Figure 22:
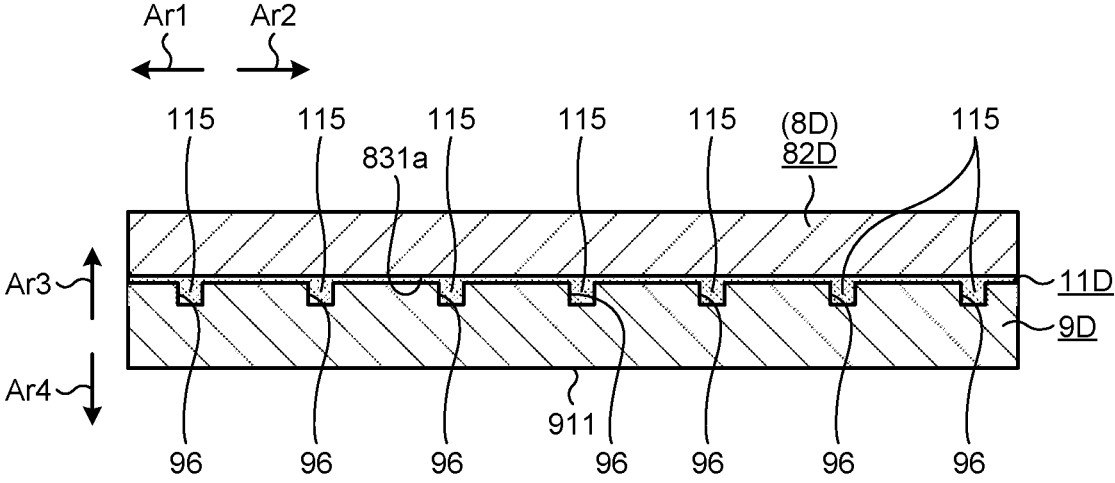
FIG. 22 is a view illustrating Modification 5-1 of the fifth embodiment.

FIGS. 21 and 22 are views illustrating Modification 5-1 of the fifth embodiment. Specifically, FIGS. 21 and 22 are cross-sectional views of the wiper jaw 82D, the resin pad 9D, and the heat transmitter 11D according to the present Modification 5-1 as viewed along the width direction, and sequentially illustrate the installation method of the resin pad 9D and the heat transmitter 11D with respect to the wiper jaw 82D.

In the above-described fifth embodiment, a plurality of coupling holes 96 may be provided on the surface of the resin pad 9D facing the bottom surface 831a as in the present Modification 5-1 illustrated in FIGS. 21 and 22.

As illustrated in FIG. 21 or 22, the coupling hole 96 linearly extends from a surface of the resin pad 9D facing the bottom surface 831a toward the gripping surface 911. Then, the plurality of coupling holes 96 are arranged side by side along the longitudinal direction of the resin pad 9D.

In addition, as illustrated in FIG. 21 or 22, the heat transmitter 11D according to the present Modification 5-1 is different from the heat transmitter 11D described in the above-described fifth embodiment in that a plurality of ridge portions 115 are provided.

The ridge portion 115 is a portion that linearly protrudes from the other plate surface (the plate surface on which the protrusion 114 is provided) of the abutment portion 113 toward the resin pad 9D and is fitted into the coupling hole 96. Then, the plurality of ridge portions 115 are arranged side by side along the longitudinal direction of the heat transmitter 11D.

Then, in the present Modification 5-1, the worker uses the elasticity of the resin pad 9D to screw the resin pad 9D from the lower side to the upper side in FIGS. 21 and 22 until the pair of claws 831d enter the pair of slits 92, the protrusion 114 enters the groove portion 95, and the plurality of ridge portions 115 enter the plurality of coupling holes 96.

Sixth Embodiment

Next, the present sixth embodiment will be described.

In the following description, the same reference numerals are given to the same configurations as those of the above-described first embodiment, and a detailed description thereof will be omitted or simplified.

The present sixth embodiment is different from the above-described first embodiment in the attachment structure of the resin pad 9 to the jaw 8. Hereinafter, for convenience of description, the jaw 8 and the wiper jaw 82 according to the present sixth embodiment are referred to as a jaw 8E and a wiper jaw 82E, respectively. In addition, the resin pad 9 according to the present sixth embodiment will be referred to as a resin pad 9E.

Figure 23:
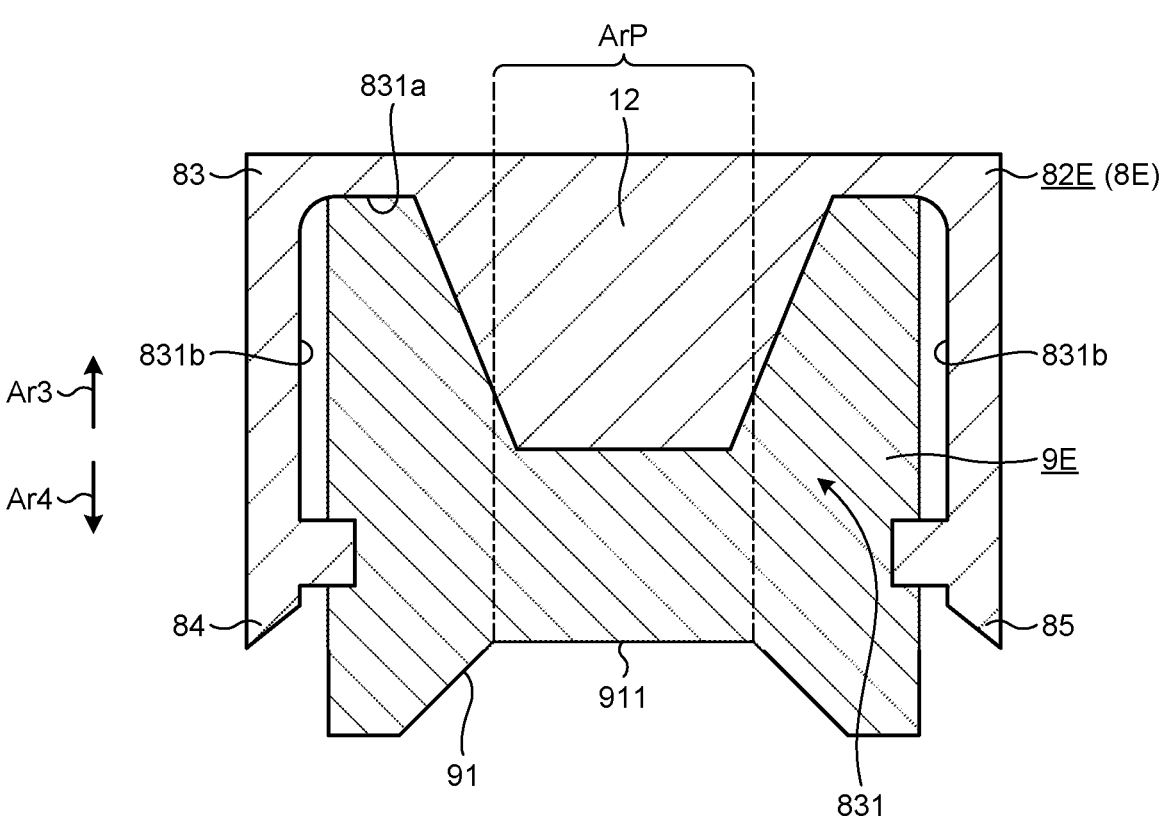
FIG. 23 is a view illustrating an attachment structure of a resin pad to a jaw according to a sixth embodiment.

FIG. 23 is a view illustrating an attachment structure of the resin pad 9E to the jaw 8E according to the sixth embodiment. Specifically, FIG. 23 is a cross-sectional view corresponding to FIG. 9.

In the present sixth embodiment, the heat transmitter 11 described in the above-described first embodiment is omitted.

The jaw 8E is different from the jaw 8 described in the above-described first embodiment in that the wiper jaw 82E having a different shape from the wiper jaw 82 is adopted.

As illustrated in FIG. 23, the wiper jaw 82E is different from the wiper jaw 82 described in the above-described first embodiment in that the pair of claws 831d described in the above-described second embodiment and a heat receiving portion 12 are provided.

The heat receiving portion 12 is a portion that receives heat of the resin pad 9. The heat receiving portion 12 protrudes downward from the bottom surface 831a in FIG. 23 and extends along the longitudinal direction of the wiper jaw 82E. In the present sixth embodiment, as illustrated in FIG. 23, the heat receiving portion 12 has a trapezoidal cross-sectional shape in which a proximal end coupled to the bottom surface 831a and a tip end are parallel to each other. More specifically, in the heat receiving portion 12, a cross-sectional area of the proximal end coupled to the bottom surface 831a is larger than an area of the tip end.

Then, the resin pad 9E according to the present sixth embodiment is provided inside the second recess 831 by insert-molding so as to follow the inner surface of the second recess 831. In this state, the central portion of the heat receiving portion 12 in the width direction is positioned in the projection area ArP as illustrated in FIG. 23.

In the present sixth embodiment, the heat receiving portion 12 has an entire length substantially equal to the entire length of the wiper jaw 82E in the longitudinal direction, but the disclosure is not limited thereto, and the heat receiving portion 12 may be present more than half of the entire length of the wiper jaw 82E in the longitudinal direction. In addition, when the wiper jaw 82E has a curved portion, the heat receiving portion 12 preferably extends over the entire length of the curved portion.

Even in the case of adopting the structure in the present sixth embodiment described above, the same effects as those of the above-described first embodiment are obtained.

In addition, in the heat receiving portion 12, the cross-sectional area of the proximal end coupled to the bottom surface 831*a* is larger than the area of the tip end. That is, in the heat receiving portion 12, a path for moving the heat received from the resin pad 9E at the tip end toward the proximal end coupled to the bottom surface 831*a* is widened. Therefore, the heat of the resin pad 9 can be effectively received by the heat receiving portion 12, and the dissipation efficiency of heat from the resin pad 9 can be improved.

Modification 6-1 of Sixth Embodiment

Figure 24:
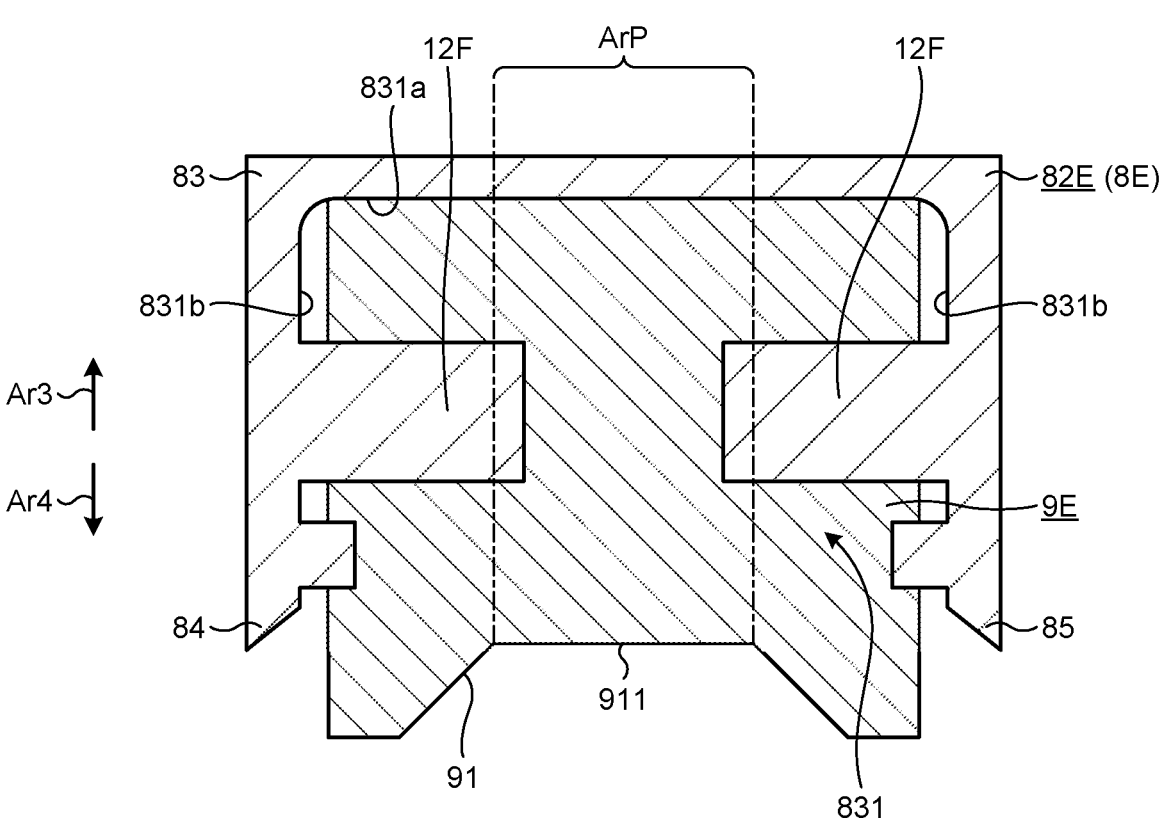
FIG. 24 is a view illustrating Modification 6-1 of the sixth embodiment.

FIG. 24 is a view illustrating Modification 6-1 of the sixth embodiment. Specifically, FIG. 24 is a cross-sectional view corresponding to FIG. 23.

In the above-described sixth embodiment, instead of the heat receiving portion 12, a pair of heat receiving portions 12F according to the present Modification 6-1 illustrated in FIG. 24 may be adopted.

As illustrated in FIG. 24, each of the pair of heat receiving portions 12F is positioned closer to the bottom surface 831*a* side than the pair of claws 831*d* in each of the side wall portions 831*b*, and has a rectangular cross-sectional shape linearly protruding in directions approaching each other from positions facing each other along the width direction. Then, the pair of heat receiving portions 12F extend along the longitudinal direction of the wiper jaw 82E respectively.

Then, also in the present Modification 6-1, the resin pad 9E is provided inside the second recess 831 by insert-molding so as to follow the inner surface of the second recess 831 as in the above-described sixth embodiment. In this state, the tip end portions of the pair of heat receiving portions 12F are positioned in the projection area ArP as illustrated in FIG. 23.

Even in a case where the structure of the present Modification 6-1 described above is adopted, the same effects as those of the above-described sixth embodiment are obtained.

In addition, by configuring the pair of heat receiving portions 12F as described above, the pair of heat receiving portions 12F can also function as a stopper for the resin pad 9E.

Modification 6-2 of Sixth Embodiment

Figure 25:
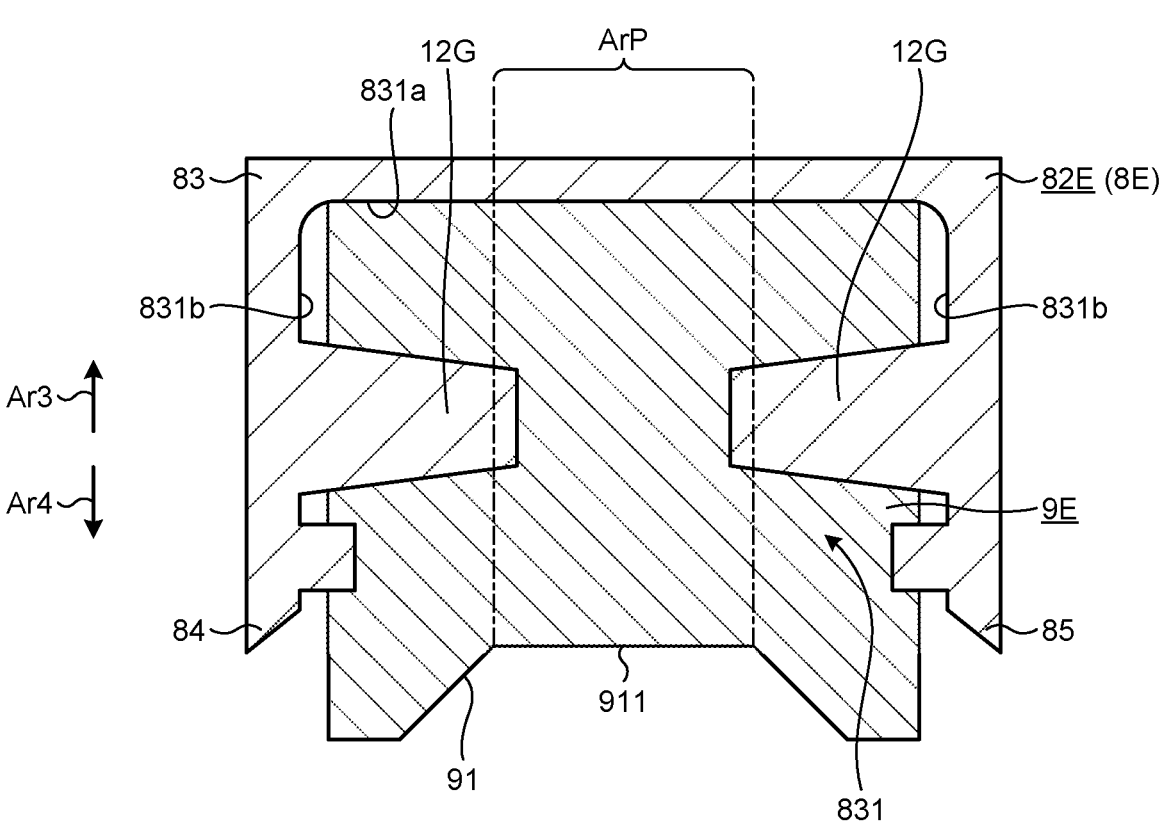
FIG. 25 is a view illustrating Modification 6-2 of the sixth embodiment.

FIG. 25 is a view illustrating Modification 6-2 of the sixth embodiment. Specifically, FIG. 25 is a cross-sectional view corresponding to FIG. 23.

In the above-described sixth embodiment, instead of the heat receiving portion 12, a pair of heat receiving portions 12G according to the present Modification 6-2 illustrated in FIG. 25 may be adopted.

As illustrated in FIG. 25, the pair of heat receiving portions 12G are obtained by changing the shape of the pair of heat receiving portions 12F according to the above-described Modification 6-1. Specifically, the heat receiving portion 12G has a trapezoidal cross-sectional shape in which a proximal end coupled to the side wall portion 831*b* and a tip end are parallel to each other, and is formed such that an area of the tip end is smaller than a cross-sectional area of the proximal end. Similarly to the heat receiving portions 12F, the tip end portions of the pair of heat receiving portions 12G are positioned in the projection area ArP.

Even in a case where the structure of the present Modification 6-2 described above is adopted, the same effects as those of the sixth embodiment and Modification 6-1 described above are obtained.

Modification 6-3 of Sixth Embodiment

Figure 26:
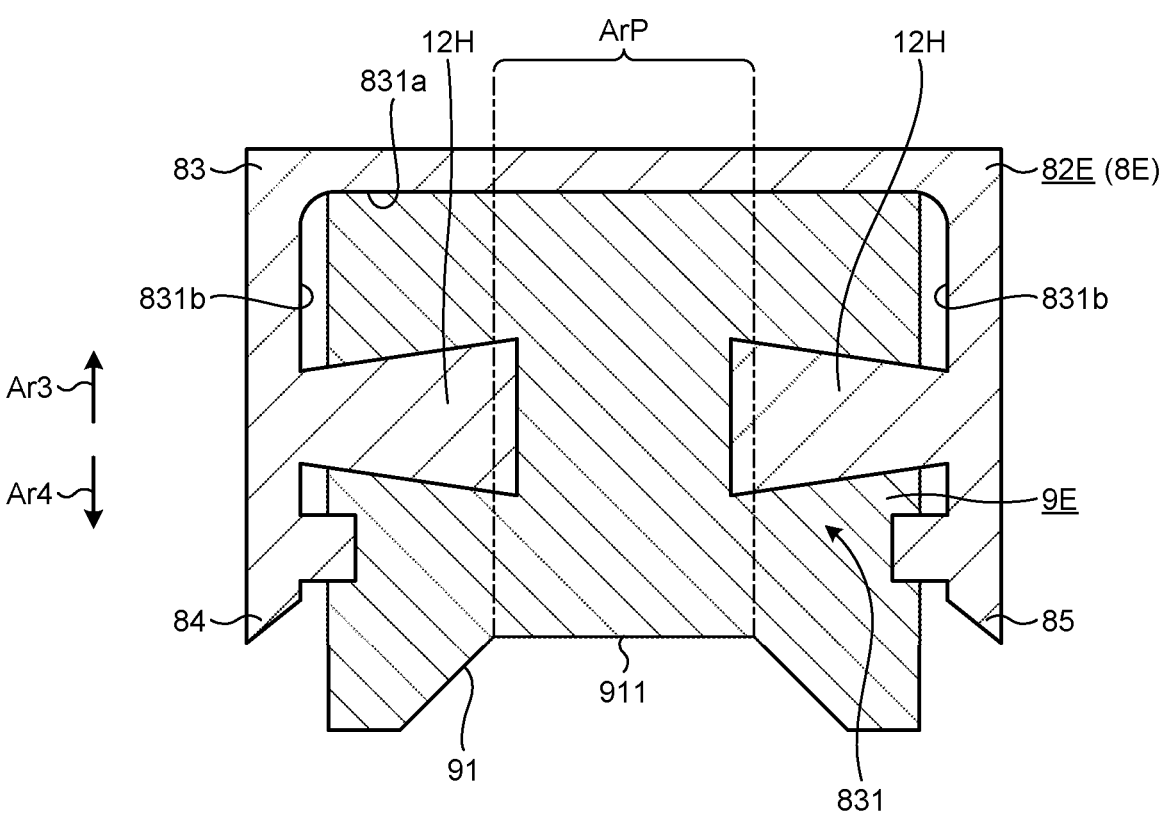
FIG. 26 is a view illustrating Modification 6-3 of the sixth embodiment.

FIG. 26 is a view illustrating Modification 6-3 of the sixth embodiment. Specifically, FIG. 26 is a cross-sectional view corresponding to FIG. 23.

In the above-described sixth embodiment, instead of the heat receiving portion 12, a pair of heat receiving portions 12H according to the present Modification 6-3 illustrated in FIG. 26 may be adopted.

As illustrated in FIG. 26, the pair of heat receiving portions 12H are obtained by changing the shape of the pair of heat receiving portions 12F according to the above-described Modification 6-1. Specifically, the heat receiving portion 12H has a trapezoidal cross-sectional shape in which a proximal end coupled to the side wall portion 831*b* and a tip end are parallel to each other, and is formed such that an area of the tip end is larger than a cross-sectional area of the proximal end. Similarly to the heat receiving portions 12F, the tip end portions of the pair of heat receiving portions 12H are positioned in the projection area ArP.

Even in a case where the structure of the present Modification 6-3 described above is adopted, the same effects as those of the above-described Modification 6-1 are obtained.

In addition, the heat receiving portion 12H is formed such that the area of the tip end is larger than the cross-sectional area of the proximal end coupled to the side wall portion 831*b*. That is, by increasing the area of the tip end, the heat receiving area from the resin pad 9E can be increased, the heat of the resin pad 9E can be effectively received by the heat receiving portion 12, and the dissipation efficiency of heat from the resin pad 9E can be improved.

Modification 6-4 of Sixth Embodiment

Figure 27:
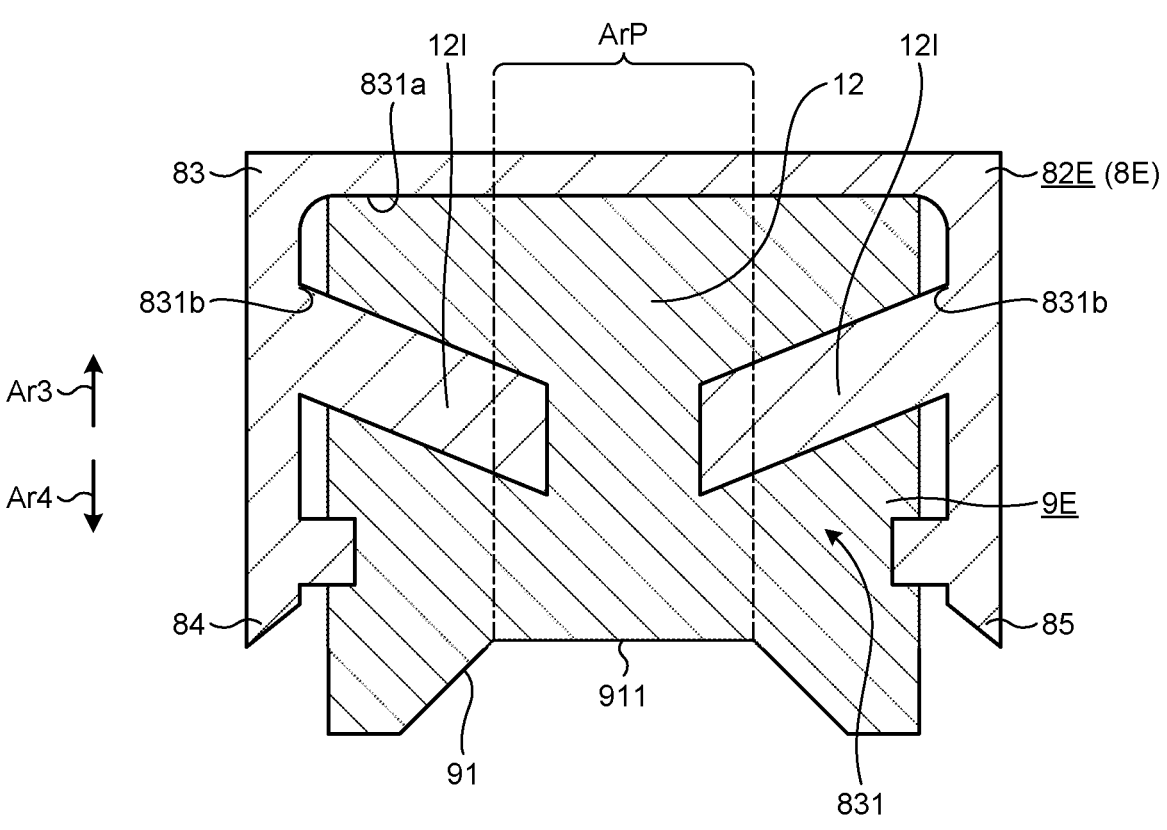
FIG. 27 is a view illustrating Modification 6-4 of the sixth embodiment.

FIG. 27 is a view illustrating Modification 6-4 of the sixth embodiment. Specifically, FIG. 27 is a cross-sectional view corresponding to FIG. 23.

In the above-described sixth embodiment, instead of the heat receiving portion 12, a pair of heat receiving portions 12I according to the present Modification 6-4 illustrated in FIG. 27 may be adopted.

As illustrated in FIG. 27, the pair of heat receiving portions 12I are obtained by changing the shape of the pair of heat receiving portions 12F according to the above-described Modification 6-1. Specifically, the heat receiving portion 12I has a cross-sectional parallelogram shape inclined in a direction away from the bottom surface 831*a* from the proximal end coupled to the side wall portion 831*b* toward the tip end. Similarly to the heat receiving portions 12F, the tip end portions of the pair of heat receiving portions 12I are positioned in the projection area ArP.

Even in a case where the structure of the present Modification 6-4 described above is adopted, the same effects as those of the above-described Modification 6-1 are obtained.

In addition, the heat receiving portion 12I protrudes from the side wall portion 831*b* toward the gripping surface 911. That is, the tip end of the heat receiving portion 12I is brought close to the gripping surface 911. Therefore, the heat of the resin pad 9E can be effectively received by the heat receiving portion 12, and the dissipation efficiency of heat from the resin pad 9E can be improved.

Modification 6-5 of Sixth Embodiment

Figure 28:
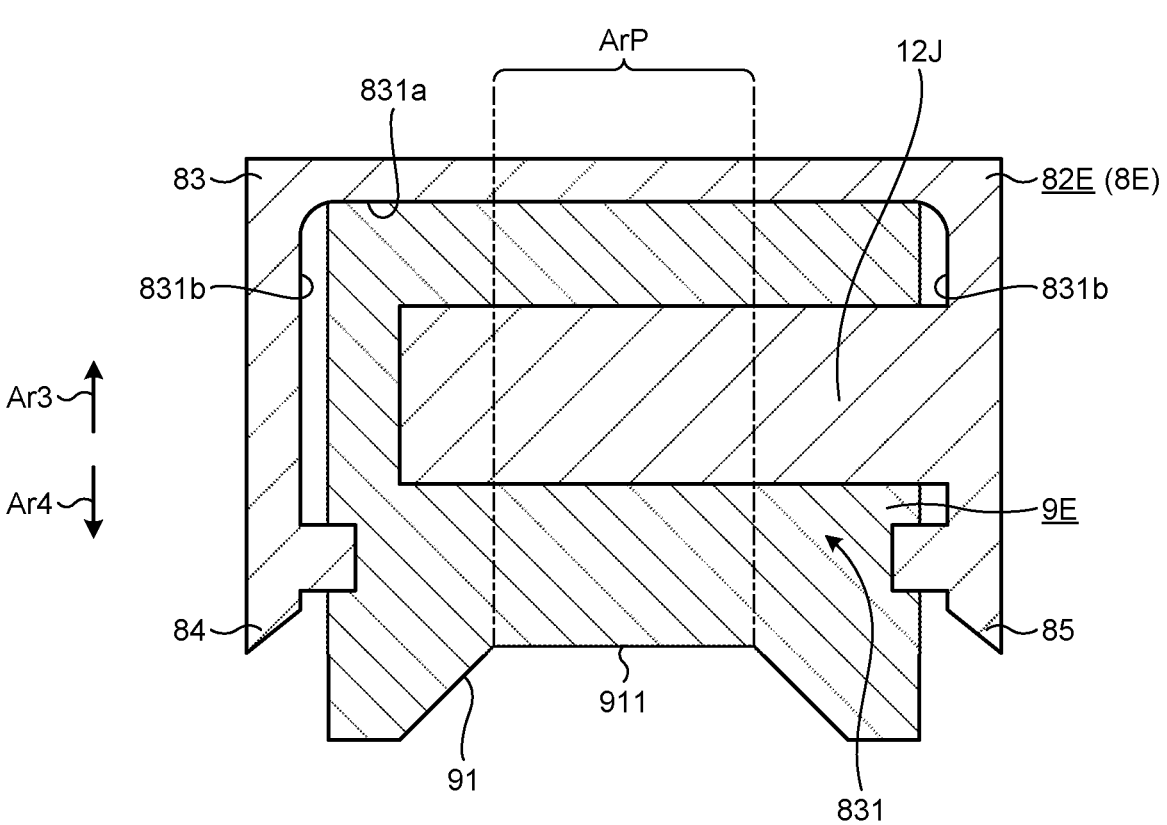
FIG. 28 is a view illustrating Modification 6-5 of the sixth embodiment.

FIG. 28 is a view illustrating Modification 6-5 of the sixth embodiment. Specifically, FIG. 28 is a cross-sectional view corresponding to FIG. 23.

In the above-described sixth embodiment, instead of the heat receiving portion 12, a heat receiving portion 12J according to the present Modification 6-5 illustrated in FIG. 28 may be adopted.

As illustrated in FIG. 28, the heat receiving portion 12J corresponds to one of the pair of heat receiving portions 12F according to the above-described Modification 6-1, and is obtained by changing the shape of the one heat receiving portion 12F. Specifically, the heat receiving portion 12J has a rectangular cross-sectional shape extending linearly from one side wall portion 831b to a position close to the other side wall portion 831b across the projection area ArP.

Even in a case where the structure of the present Modification 6-5 described above is adopted, the same effects as those of the above-described Modification 6-1 are obtained.

Modification 6-6 of Sixth Embodiment

Figure 29:
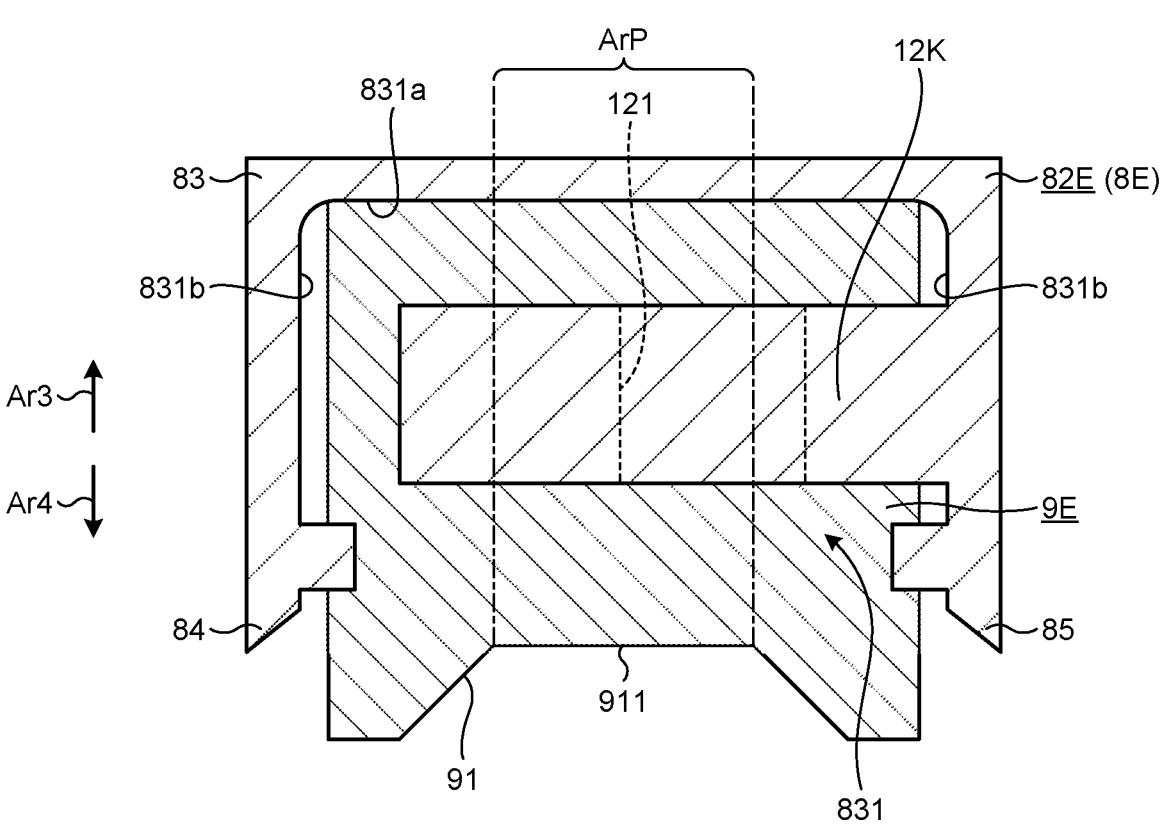
FIG. 29 is a view illustrating Modification 6-6 of the sixth embodiment.

FIG. 29 is a view illustrating Modification 6-6 of the sixth embodiment. Specifically, FIG. 29 is a cross-sectional view corresponding to FIG. 23.

In the above-described sixth embodiment, instead of the heat receiving portion 12, a heat receiving portion 12K according to the present Modification 6-6 illustrated in FIG. 29 may be adopted.

As illustrated in FIG. 29, the heat receiving portion 12K is different from the heat receiving portion 12J according to the above-described Modification 6-5 in that a through-hole 121 is provided.

The through-hole 121 is a hole penetrating from the treatment portion side Ar4 to the back surface side Ar3 in the heat receiving portion 12K. In the present Modification 6-6, as illustrated in FIG. 29, a portion of the through-hole 121 is positioned in the projection area ArP. Then, a plurality of the through-holes 121 are provided and arranged side by side along the longitudinal direction.

Even in a case where the structure of the present Modification 6-6 described above is adopted, the same effects as those of the above-described Modification 6-5 are obtained.

In addition, the heat receiving portion 12K is provided with the above-described through-hole 121. Therefore, when the resin pad 9E is insert-molded, the resin material constituting the resin pad 9E easily flows, and the insert-molding is facilitated.

Modification 6-7 of Sixth Embodiment

Figure 30:
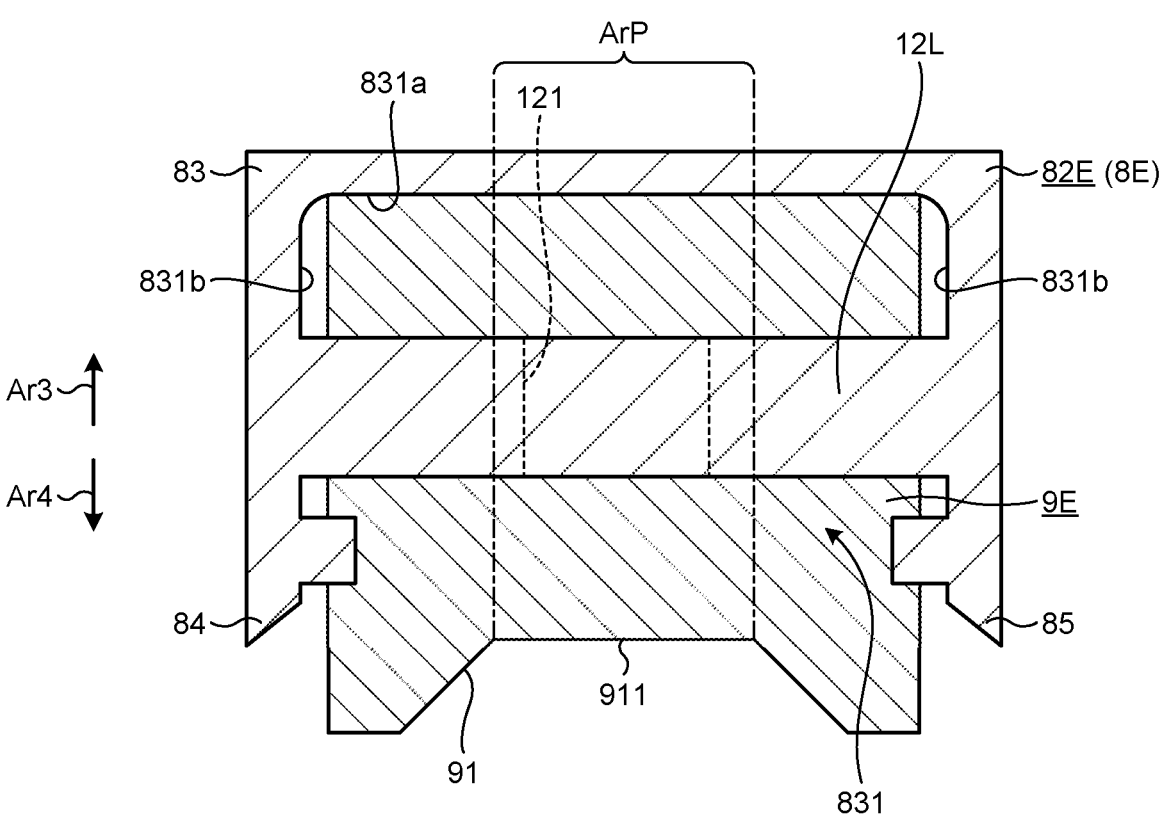
FIG. 30 is a view illustrating Modification 6-7 of the sixth embodiment.

FIG. 30 is a view illustrating Modification 6-7 of the sixth embodiment. Specifically, FIG. 30 is a cross-sectional view corresponding to FIG. 23.

In the above-described sixth embodiment, instead of the heat receiving portion 12, a heat receiving portion 12L according to the present Modification 6-7 illustrated in FIG. 30 may be adopted.

As illustrated in FIG. 30, the heat receiving portion 12L is formed by connecting tip end portions of the pair of heat receiving portions 12F according to the above-described Modification 6-1. In addition, similarly to the above-described Modification 6-6, the heat receiving portion 12L is provided with the through-hole 121. In the present Modification 6-7, the through-hole 121 is positioned in the projection area ArP.

Even in a case where the structure of the present Modification 6-7 described above is adopted, the same effects as those of the above-described Modification 6-6 are obtained.

Modification 6-8 of Sixth Embodiment

Figure 31:
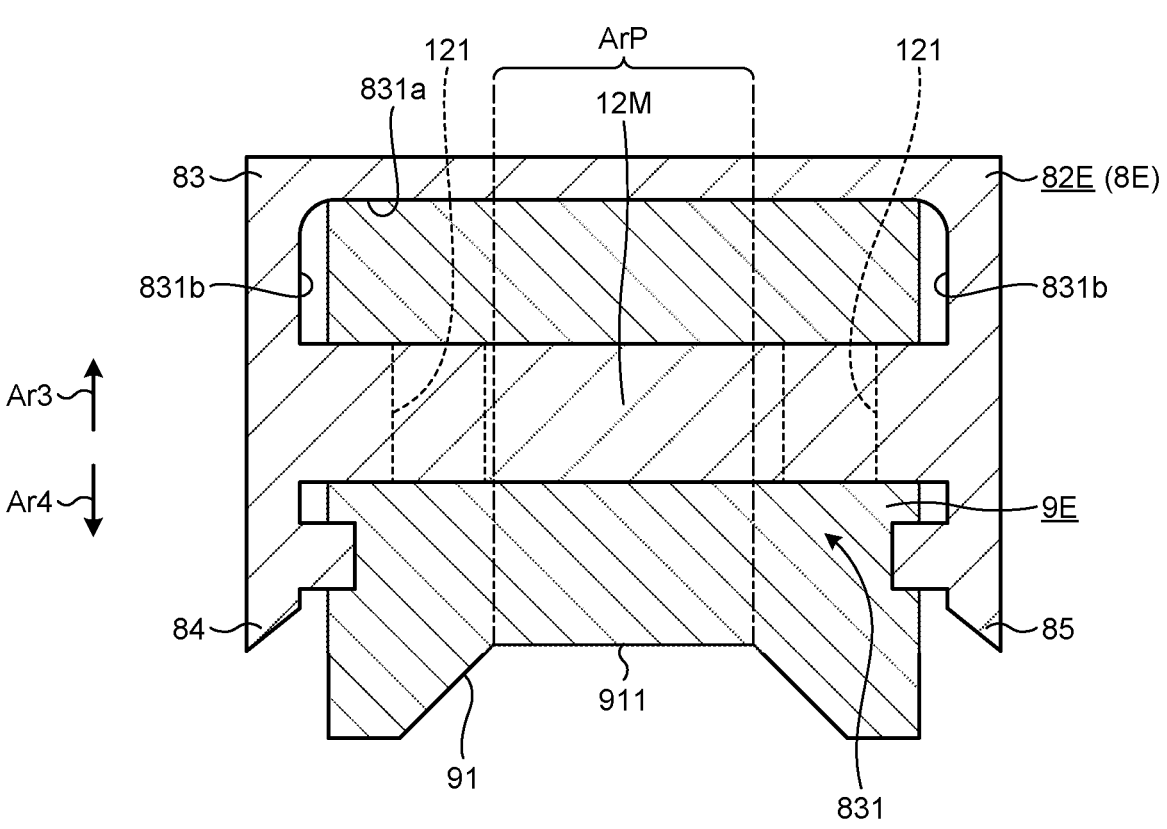
FIG. 31 is a view illustrating Modification 6-8 of the sixth embodiment.

FIG. 31 is a view illustrating Modification 6-8 of the sixth embodiment. Specifically, FIG. 31 is a view corresponding to FIG. 23.

In the above-described sixth embodiment, instead of the heat receiving portion 12, a heat receiving portion 12M according to the present Modification 6-8 illustrated in FIG. 31 may be adopted.

As illustrated in FIG. 31, the heat receiving portion 12M is different from the heat receiving portion 12L according to the above-described Modification 6-7 in that a formation position of the through-hole 121 is changed. In the present Modification 6-8, the through-hole 121 is provided at a position avoiding the projection area ArP.

Even in a case where the structure of the present Modification 6-8 described above is adopted, the same effects as those of the above-described Modification 6-7 are obtained.

In addition, the through-hole 121 is provided at a position avoiding the projection area ArP where frictional heat generated on the gripping surface 911 is easily transferred in the resin pad 9E. Therefore, the heat of the resin pad 9E can be effectively received by the heat receiving portion 12M, and the dissipation efficiency of heat from the resin pad 9E can be improved.

Modification 6-9 of Sixth Embodiment

Figure 32:
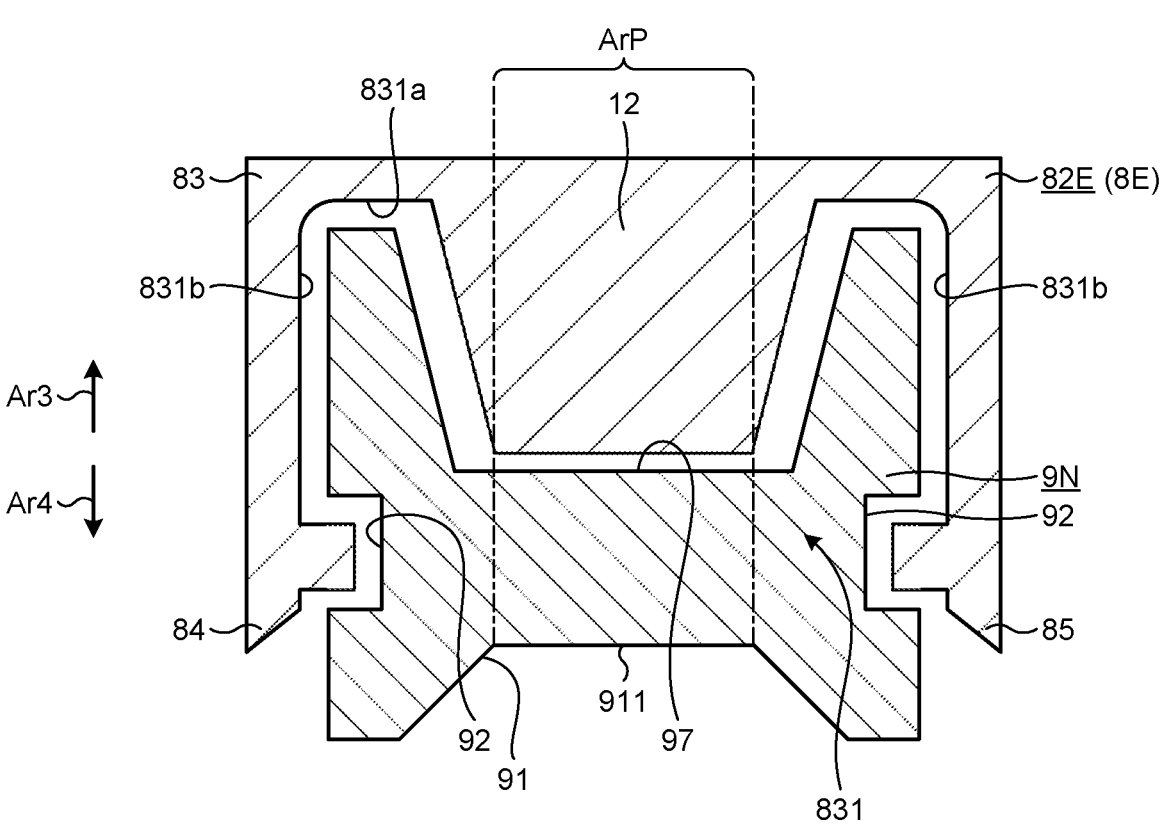
FIG. 32 is a view illustrating Modification 6-9 of the sixth embodiment.

FIG. 32 is a view illustrating Modification 6-9 of the sixth embodiment. Specifically, FIG. 32 is a view corresponding to FIG. 23.

In the above-described sixth embodiment, the resin pad 9E is provided inside the second recess 831 by insert-molding, but the disclosure is not limited thereto.

In the above-described sixth embodiment, instead of the resin pad 9E, a resin pad 9N according to the present Modification 6-9 illustrated in FIG. 32 may be adopted.

As illustrated in FIG. 32, the resin pad 9N is different from the resin pad 9E described in the above-described sixth embodiment in that the pair of slits 92 described in the above-described second embodiment and a groove portion 97 are provided.

The groove portion 97 is provided on a surface of the resin pad 9N facing the bottom surface 831a, and has an inner surface shape corresponding to the outer shape of the heat receiving portion 12.

Then, the resin pad 9N is slid along the longitudinal direction of the wiper jaw 82E in a state where the pair of claws 831d enter the pair of slits 92 and the heat receiving portion 12 enters the groove portion 97 inside the second recess 831. As a result, the resin pad 9N is attached to the wiper jaw 82E. That is, a clearance is provided between the resin pad 9N (groove portion 97) and the heat receiving portion 12. Then, in the heat receiving portion 12, when the living tissue is gripped between the treatment portion 101 and the resin pad 9N, the clearance decreases, whereby a heat transfer path is generated between the heat receiving portion 12 and the resin pad 9N.

The installation method of the resin pad 9N is not limited to the sliding method described above. For example, by using the elasticity of the resin pad 9N, an installation method in which the resin pad 9A is screwed until the pair of claws 831d enter the pair of slits 92 from the lower side to the upper side in FIG. 32 may be adopted.

Even in a case where the structure of the present Modification 6-9 described above is adopted, the same effects as those of the above-described sixth embodiment are obtained.

OTHER EMBODIMENTS

Although the embodiments for carrying out the disclosure have been described so far, the disclosure should not be limited only by the above-described first to sixth embodiments.

Modification 7-1 of First to Sixth Embodiments

In the above-described first embodiment, the shapes of the jaw 8 (wiper jaw 82) and the resin pad 9 may be changed as in the present Modification 7-1. Hereinafter, for convenience of description, the jaw 8 and the wiper jaw 82 according to the present Modification 7-1 are referred to as a jaw 8O and a wiper jaw 820, respectively. In addition, the resin pad 9 according to the present Modification 7-1 will be referred to as a resin pad 9O. In the other second to sixth embodiments as well, the jaw 8O (wiper jaw 820) and the resin pad 9O may be adopted.

Figure 33:
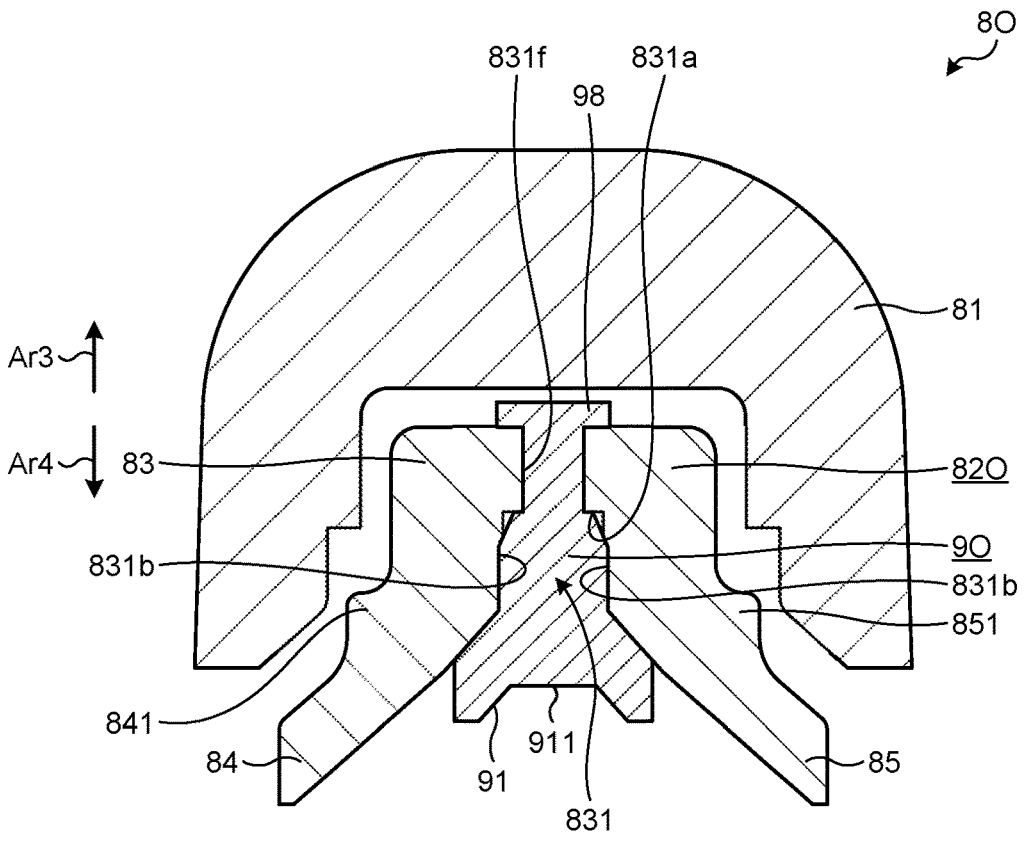
FIG. 33 is a view illustrating Modification 7-1 of the first to sixth embodiments.

FIG. 33 is a view illustrating Modification 7-1 of the first to sixth embodiments. Specifically, FIG. 33 is a view illustrating an attachment structure of the resin pad 9O to the jaw 8O according to Modification 7-1. More specifically, FIG. 33 is a cross-sectional view of the resin pad 9O and the jaw 8O taken along a plane orthogonal to the longitudinal direction of the jaw 8O. In FIG. 33, for convenience of explanation, the arm 81 and the resin cover RC in the jaw 8O are illustrated as one member.

The jaw 8O is different from the jaw 8 described in the above-described first embodiment in that the wiper jaw 820 having a different shape from the wiper jaw 82 is adopted.

As illustrated in FIG. 33, the wiper jaw 820 is different from the wiper jaw 82 described in the above-described first embodiment in that a seventh insertion hole 831*f* and first and second bulging portions 841 and 851 are provided.

The seventh insertion hole 831*f* penetrates from the outer surface of the wiper jaw body 83 on the back surface side Ar3 to the inside of the second recess 831.

The first bulging portion 841 is a portion bulging from a surface of the first tooth portion 84 on the back surface side Ar3 toward the back surface side Ar3.

The second bulging portion 851 is a portion bulging from a surface of the second tooth portion 85 on the back surface side Ar3 toward the back surface side Ar3.

As illustrated in FIG. 33, the resin pad 9O is different from the resin pad 9 described in the above-described first embodiment in that a coupling portion 98 is provided.

The coupling portion 98 is a portion that protrudes from a surface facing the bottom surface 831*a* toward the back surface side Ar3 and is coupled to the wiper jaw 820.

The resin pad 9O described above is attached to the wiper jaw 820 as described below.

That is, the worker press-fits the resin pad 9O into the second recess 831 while inserting the coupling portion 98 into the seventh insertion hole 831*f*. Then, the worker thermally caulks the tip end portion of the coupling portion 98 on the back surface side Ar3 toward the treatment portion side Ar4. As a result, the resin pad 9O is attached to the wiper jaw 820.

According to the present Modification 7-1 described above, the following effects are obtained.

In the structure according to the present Modification 7-1, when the living tissue is gripped between the resin pad 9O and the treatment portion 101 and the wiper jaw 820 is swung with respect to the arm 81, the tip end portion of the coupling portion 98 on the back surface side Ar3 abuts on the surface of the arm 81 on the treatment portion side Ar4. As a result, it is possible to secure a heat transfer path from the resin pad 9O to the arm 81 in addition to the heat transfer path from the resin pad 9O to the wiper jaw 820.

In addition, when the living tissue is treated in a state where the living tissue is gripped between the resin pad 9O and the treatment portion 101, in a case where the resin pad 9O has a high temperature, the tip end portion of the coupling portion 98 on the back surface side Ar3 is further crushed by heat and gripping force. As a result, the entire wiper jaw 820 moves to the back surface side Ar3, and an overload state can be avoided.

Furthermore, by providing the first and second bulging portions 841 and 851 in the wiper jaw 820, a heat capacity of the wiper jaw 820 can be increased, and the dissipation efficiency of heat from the resin pad 9O can be improved.

In addition, the resin pad 9O is attached to the wiper jaw 820 by thermal caulking. Therefore, it is not necessary to provide a structure for holding the resin pad in the wiper jaw 820, and the structure of the wiper jaw 820 can be simplified.

Modification 7-2 of First to Sixth Embodiments

In the above-described first embodiment, the shape of the jaw 8 may be changed as in the present Modification 7-2. Hereinafter, for convenience of description, the jaw 8, the arm 81, and the wiper jaw 82 according to the present Modification 7-2 are referred to as a jaw 8P, an arm 81P, and a wiper jaw 82P, respectively. In the other second to sixth embodiments as well, the jaw 8P may be adopted.

Figure 34:
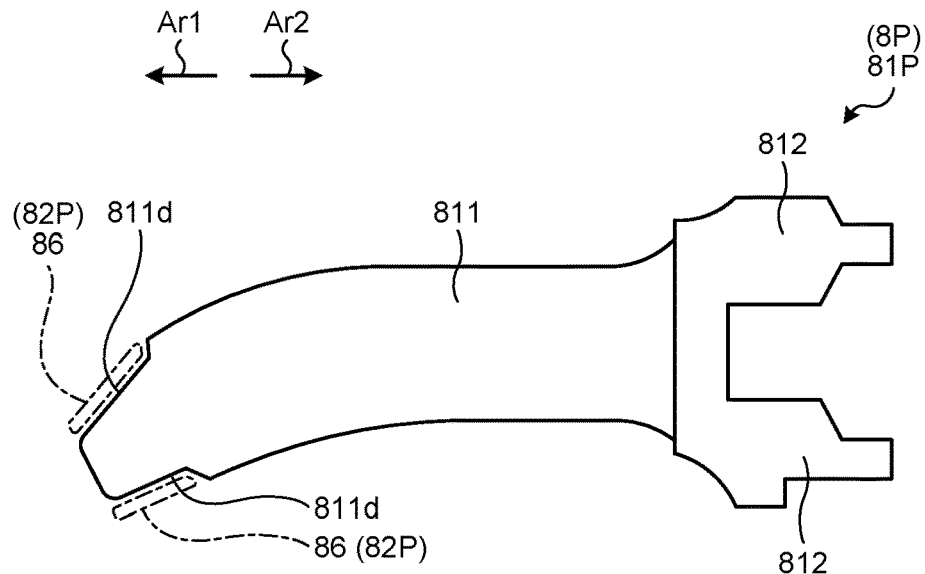
FIG. 34 is a view illustrating Modification 7-2 of the first to sixth embodiments.

FIG. 34 is a view illustrating Modification 7-2 of the first to sixth embodiments. Specifically, FIG. 34 is a view of the jaw 8P (arm 81P) according to Modification 7-2 as viewed from the back surface side Ar3. In FIG. 34, illustration of the resin cover RC is omitted for convenience of description.

The jaw 8P is different from the jaw 8 described in the above-described first embodiment in that the arm 81P and the wiper jaw 82P having different shapes from the arm 81 and the wiper jaw 82 are adopted.

As illustrated in FIG. 34, the arm 81P is different from the arm 81 described in the above-described first embodiment in that a pair of notch portions 811*d* are provided.

As illustrated in FIG. 34, the pair of notch portions 811*d* are provided by cutting out a corner portion of an end portion of the arm body 811 on the distal end side Art.

As illustrated in FIG. 34, the wiper jaw 82P is different from the wiper jaw 82 described in the above-described first embodiment in that a pair of thick portions 86 are provided.

The pair of thick portions 86 are portions provided at positions facing the pair of notch portions 811*d* and bulging toward the back surface side Ar3.

According to the present Modification 7-2 described above, the following effects are obtained.

In the structure of the present Modification 7-2, the wiper jaw 82P includes the pair of thick portions 86 described above. Therefore, the heat capacity of the end portion of the wiper jaw 82P on the distal end side Ar1 can be increased, and the dissipation efficiency of heat from the end portion of the resin pad 9 on the distal end side Ar1 can be improved by the pair of thick portions 86.

Modification 7-3 of First to Sixth Embodiments

FIG. 35 is a view illustrating Modification 7-3 of the first to sixth embodiments. Specifically, FIG. 35 is a cross-sectional view obtained by cutting the distal end portion of an ultrasonic treatment instrument 1Q according to the present Modification 7-3 by a plane including the central axis Ax of the sheath 7. In FIG. 35, illustration of the jaw 8 is omitted for convenience of description.

In the above-described first embodiment, a heat diffuser 13 may be adopted as in the ultrasonic treatment instrument 1Q according to the present Modification 7-3 illustrated in FIG. 35. In the other second to sixth embodiments as well, the heat diffuser 13 may be adopted.

The heat diffuser 13 is made of graphite, copper foil, or the like, and is provided between the inner tube TI and the sheath 7 as illustrated in FIG. 35. Specifically, the heat diffuser 13 extends from the lining LI positioned closest to the distal end side Ar1 to at least one side (both sides in the example of FIG. 35) of the distal end side Ar1 and the proximal end side Ar2.

According to the present Modification 7-3 described above, the following effects are obtained.

In the structure of the present Modification 7-3, the heat diffuser 13 described above is adopted. Therefore, the heat diffuser 13 can diffuse the heat stored in the portion around the lining LI in the sheath 7 by moving along a heat transfer path of the treatment portion 101 to the shaft 102 to the lining LI and to the sheath 7.

Modification 7-4 of First to Sixth Embodiments

FIG. 36 is a view illustrating Modification 7-4 of the first to sixth embodiments. Specifically, FIG. 36 is a cross-sectional view corresponding to FIG. 35.

In the above-described first embodiment, a heat diffuser 13R may be adopted as in an ultrasonic treatment instrument 1R according to the present Modification 7-4 illustrated in FIG. 36. In the other second to sixth embodiments as well, the heat diffuser 13R may be adopted.

The heat diffuser 13R according to the present Modification 7-4 is made of the same material as the heat diffuser 13 according to the above-described Modification 7-3, but is disposed at a different site. As illustrated in FIG. 36, the heat diffuser 13 according to the present Modification 7-4 extends from the lining LI positioned closest to the distal end side Ar1 to at least one side (both sides in the example of FIG. 36) of the distal end side Ar1 and the proximal end side Ar2 between the outer tube TO and the sheath 7.

Even in a case where the structure of the present Modification 7-4 described above is adopted, the same effects as those of the above-described Modification 7-3 are obtained.

Modification 7-5 of First to Sixth Embodiments

Figure 37:
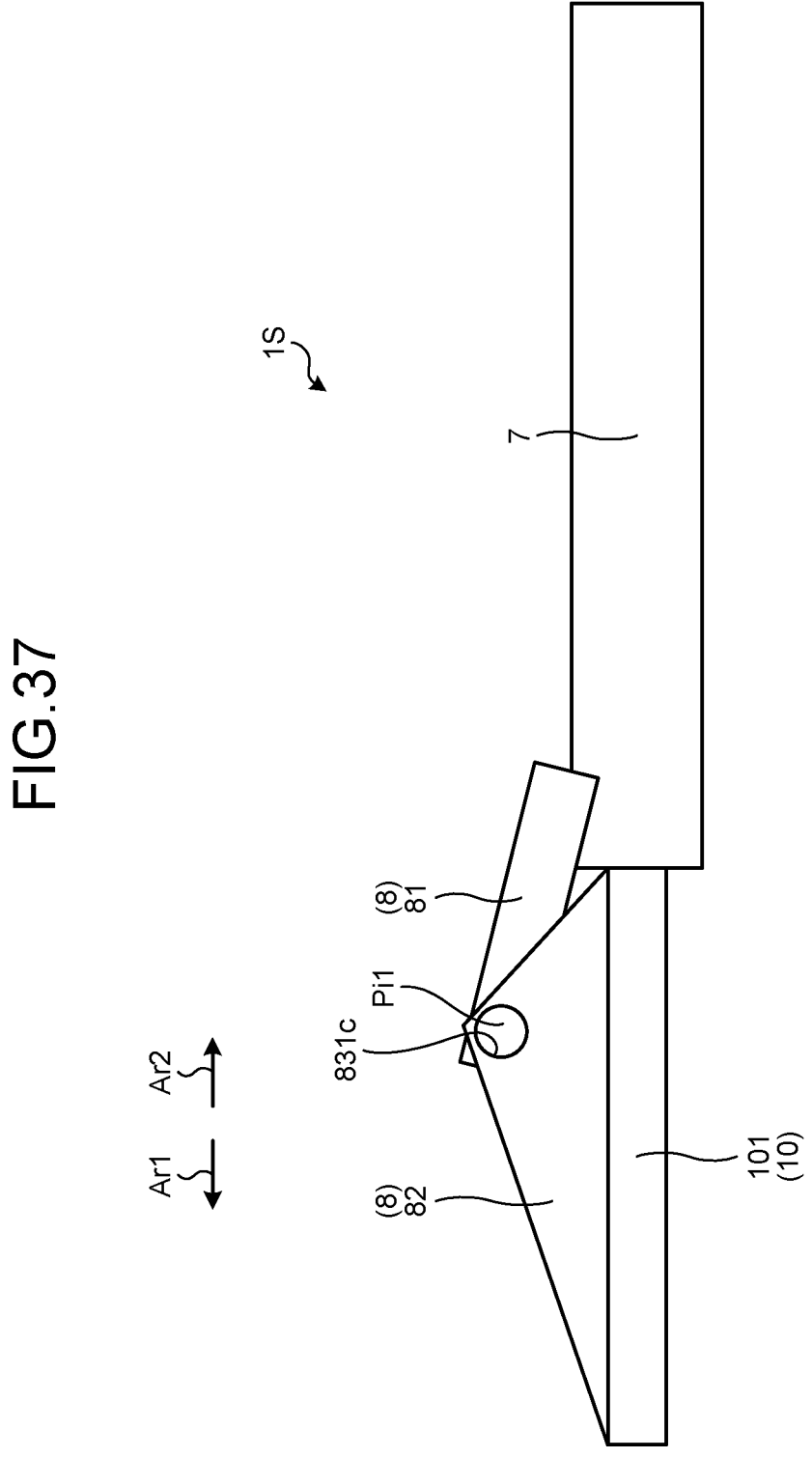
FIG. 37 is a view illustrating Modification 7-5 of the first to sixth embodiments.

FIG. 37 is a view illustrating Modification 7-5 of the first to sixth embodiments. Specifically, FIG. 37 is a view illustrating a distal end portion of an ultrasonic treatment instrument 1S according to the present Modification 7-5. In FIG. 37, illustration of the resin cover RC is omitted for convenience of description.

In the above-described first embodiment, as in the ultrasonic treatment instrument 1S according to the present Modification 7-5 illustrated in FIG. 37, the fifth insertion hole 831c may be provided closer to the proximal end side Ar2 than the center of the wiper jaw 82 in the longitudinal direction. In the other second to sixth embodiments as well, the fifth insertion hole 831c may be provided at the same position.

According to the present Modification 7-5 described above, the following effects are obtained.

In the structure of the present Modification 7-5, the fifth insertion hole 831c is provided closer to the proximal end side Ar2 than the center of the wiper jaw 82 in the longitudinal direction. Therefore, it is possible to reduce the gripping pressure applied to the living tissue on the distal end side Ar1 and to suppress deterioration of the resin pad 9 on the distal end side Ar1.

Modification 7-6 of First to Sixth Embodiments

In the above-described first embodiment, the shape of the resin pad 9 may be changed as in the present Modification 7-6. Hereinafter, for convenience of description, the resin pad 9 according to the present Modification 7-6 will be referred to as a resin pad 9T. In the other second to sixth embodiments as well, the resin pad 9T may be adopted.

Figure 38:
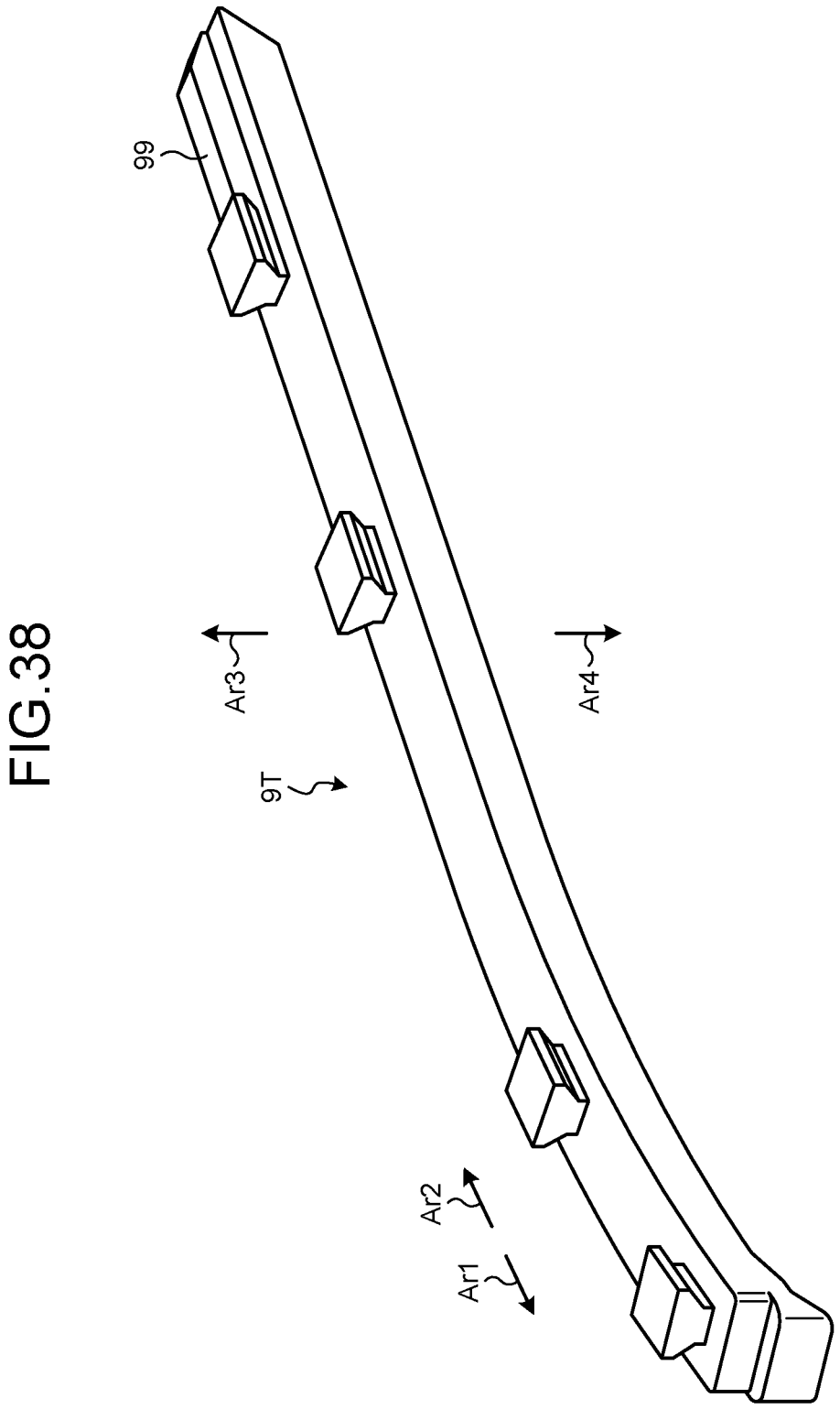
FIG. 38 is a view illustrating Modification 7-6 of the first to sixth embodiments.
Figure 39:
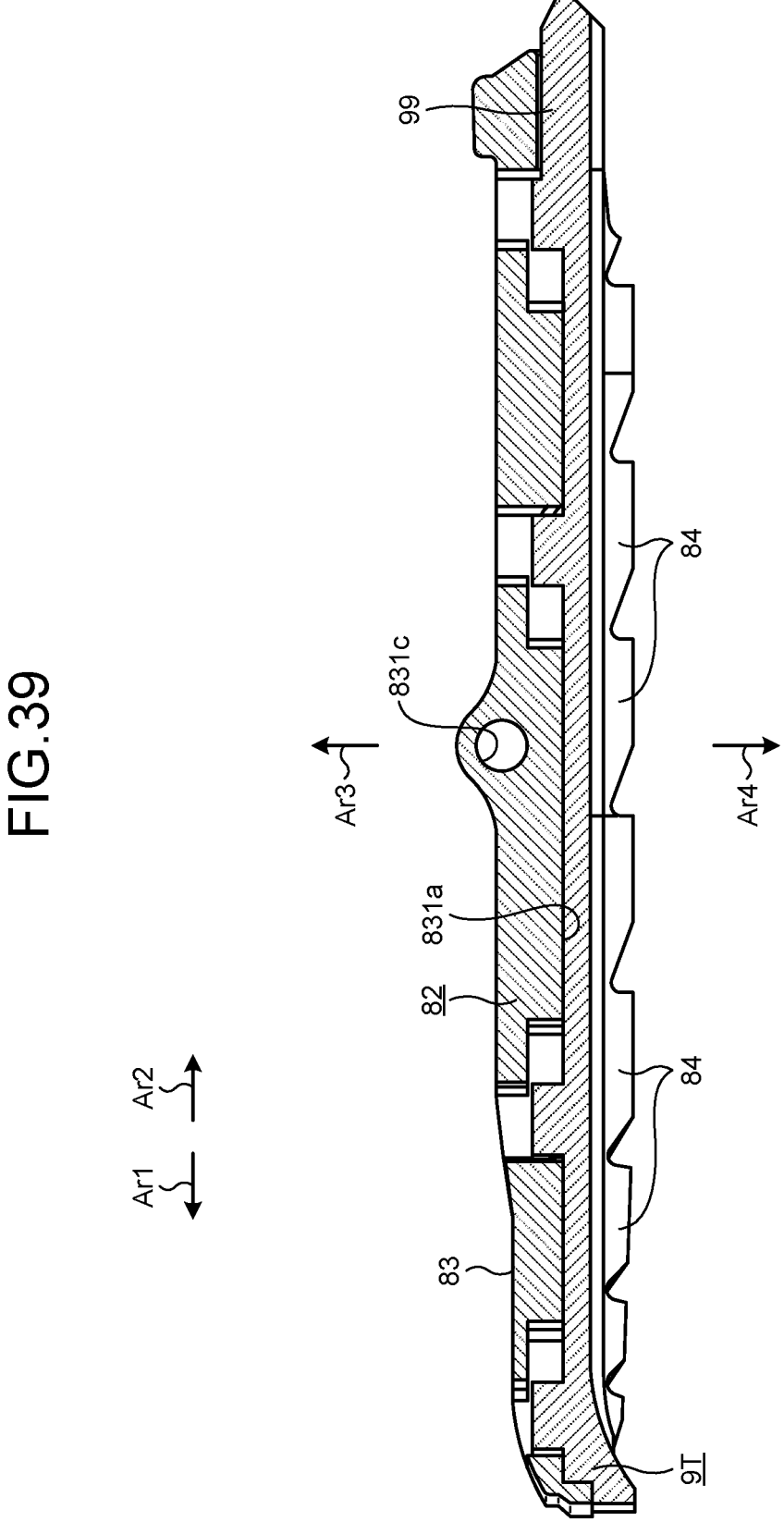
FIG. 39 is a view illustrating Modification 7-6 of the first to sixth embodiments.

FIGS. 38 and 39 are views illustrating Modification 7-6 of the first to sixth embodiments. Specifically, FIG. 38 is a perspective view of the resin pad 9T according to the present Modification 7-6 as viewed from the back surface side Ar3. FIG. 39 is a cross-sectional view of a state where the resin pad 9T is attached to the wiper jaw 82 taken along a plane orthogonal to the width direction.

As illustrated in FIG. 38 or 39, the resin pad 9T is different from the resin pad 9 described in the above-described first embodiment in that a thick portion 99 is provided.

The thick portion 99 is provided on the proximal end side Ar2 of the surface of the resin pad 9T facing the bottom surface 831a. Then, when the living tissue is gripped between the treatment portion 101 and the resin pad 9T, the thick portion 99 is pressed against the bottom surface 831a and elastically deformed by the gripping pressure applied to the living tissue.

According to the present Modification 7-6 described above, the following effects are obtained.

In the structure of the present Modification 7-6, the resin pad 9T includes the above-described thick portion 99. Therefore, it is possible to suppress non-uniformity of the gripping pressure applied to the living tissue in the longitudinal direction of the resin pad 9T.

Modification 7-7 of First to Sixth Embodiments

Figure 40:
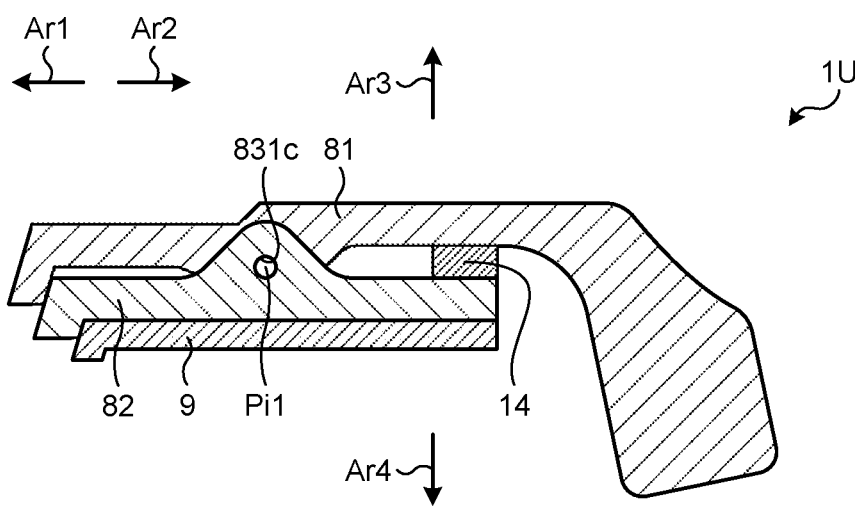
FIG. 40 is a view illustrating Modification 7-7 of the first to sixth embodiments.

FIG. 40 is a view illustrating Modification 7-7 of the first to sixth embodiments. Specifically, FIG. 40 is a cross-sectional view of the jaw 8 according to the present Modification 7-7 taken along a plane orthogonal to the width direction. In FIG. 40, illustration of the resin cover RC is omitted for convenience of description.

In the above-described first embodiment, an elastic material 14 may be adopted as in an ultrasonic treatment instrument 1U according to the present Modification 7-7 illustrated in FIG. 40. In the other second to sixth embodiments as well, the elastic material 14 may be adopted.

The elastic material 14 is configured by a material having thermal conductivity and being elastically deformable, and is provided closer to the proximal end side Ar2 than the fifth insertion hole 831c between the arm 81 and the wiper jaw 82. Then, when the living tissue is gripped between the treatment portion 101 and the resin pad 9, the elastic material 14 is crushed between the arm 81 and the wiper jaw 82 by the gripping pressure applied to the living tissue and elastically deformed.

Even in a case where the structure of the present Modification 7-7 described above is adopted, the same effects as those of the above-described Modification 7-6 are obtained.

In addition, the elastic material 14 has thermal conductivity. Therefore, the elastic material 14 can secure a heat transfer path of the wiper jaw 82 to the arm 81.

Modification 7-8 of First to Sixth Embodiments

In the above-described first embodiment, the configuration of the resin pad 9 may be changed as in the present Modification 7-8. Hereinafter, for convenience of description, the wiper jaw 82 and the resin pad 9 according to the present Modification 7-8 are referred to as a wiper jaw 82V and a resin pad 9V, respectively. In the other second to sixth embodiments, the configuration of the resin pad 9V may be adopted.

Figure 41:
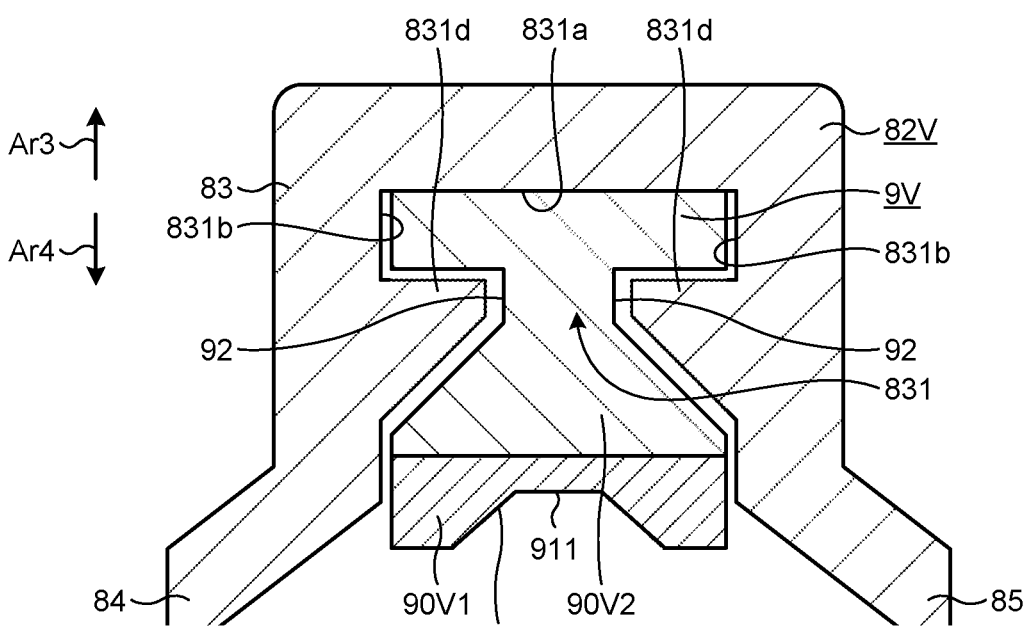
FIG. 41 is a view illustrating Modification 7-8 of the first to sixth embodiments.

FIG. 41 is a view illustrating Modification 7-8 of the first to sixth embodiments. Specifically, FIG. 41 is a cross-sectional view corresponding to FIG. 9.

As illustrated in FIG. 41, the wiper jaw 82V is similar to the wiper jaw 82A described in the above-described second embodiment.

In addition, as illustrated in FIG. 41, the resin pad 9V has the same shape as the resin pad 9A described in the above-described second embodiment. That is, similarly to the resin pad 9A described in the above-described second embodiment, the resin pad 9V is attached to the wiper jaw 82V in a state where the pair of claws 831*d* enter the pair of slits 92 inside the second recess 831.

Here, the resin pad 9V is formed by multicolor molding. In the present Modification 7-8, the resin pad 9V is formed by two-color molding, and as illustrated in FIG. 41, a first site 90V1 and a second site 90V2 are laminated from the treatment portion side Ar4 toward the back surface side Ar3.

The first site 90V1 is a site including the gripping surface 911, and is made of, for example, polytetrafluoroethylene.

The second site 90V2 is provided on the back surface side Ar3 of the first site 90V1, and is made of a material having higher thermal conductivity than the first site for example, polyether ether ketone (PEEK), or polyimide (PI).

According to the present Modification 7-8 described above, the following effects are obtained.

In the structure of the present Modification 7-8, the resin pad 9V includes the first and second sites 90V1 and described above. Therefore, frictional heat generated in the resin pad 9V (gripping surface 911) by application of ultrasonic vibration can be moved along a heat transfer path of the first site 90V1 to the second site 90V2 and to the wiper jaw 82V. Therefore, deterioration of the resin pad 9V can be suppressed.

Modification 7-9 of First to Sixth Embodiments

In the above-described first embodiment, the configuration of the resin pad 9 may be changed as in the present Modification 7-9. Hereinafter, for convenience of description, the wiper jaw 82 and the resin pad 9 according to the present Modification 7-9 are referred to as a wiper jaw 82W and a resin pad 9W, respectively. In the other second to sixth embodiments as well, the configuration of the resin pad 9W may be adopted.

Figure 42:
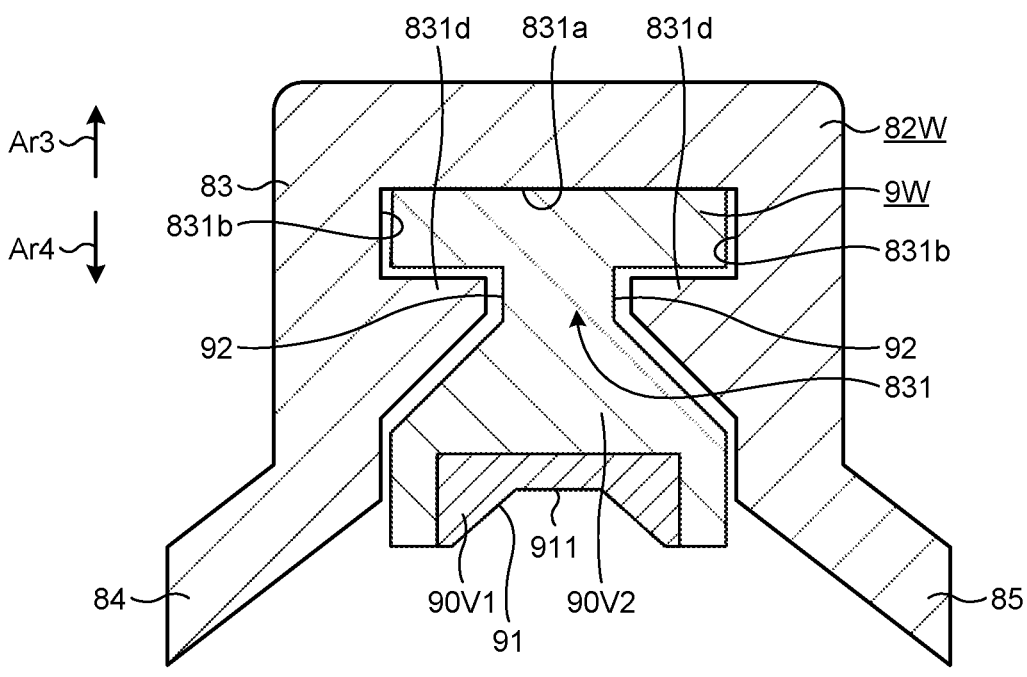
FIG. 42 is a view illustrating Modification 7-9 of the first to sixth embodiments.

FIG. 42 is a view illustrating Modification 7-9 of the first to sixth embodiments. Specifically, FIG. 42 is a view corresponding to FIG. 9.

As illustrated in FIG. 42, the wiper jaw 82W is similar to the wiper jaw 82V described in the above-described Modification 7-8.

In addition, as illustrated in FIG. 42, the resin pad 9W is similar to the resin pad 9V described in the above-described Modification 7-8. Then, in the resin pad 9W, a formation site of the second site 90V2 is different from that of the resin pad

9V. Specifically, as illustrated in FIG. 42, the second site 90V2 is also provided on both sides of the first site 90V1 in the width direction.

Even in a case where the structure of the present Modification 7-9 described above is adopted, the same effects as those of the above-described Modification 7-8 are obtained.

In addition, the second site 90V2 is also provided on both sides of the first site 90V1 in the width direction. Therefore, the heat of the first site 90V1 can also be moved to both sides in the width direction.

Modification 7-10 of First to Sixth Embodiments

In the above-described Modification 7-8 and Modification 7-9, the first and second sites 90V1 and 90V2 are made of different materials, but the disclosure is not limited thereto. For example, polytetrafluoroethylene may be used as a main material, and the first and second sites 90V1 and 90V2 may be formed by varying a content of a thermally conductive filler included in the main material. At this time, the content of the thermally conductive filler in the second site 90V2 is made larger than the content of the thermally conductive filler in the first site 90V1. In addition, as the thermally conductive filler, boron nitride, alumina, and the like can be exemplified.

Modification 7-11 of First to Sixth Embodiments

Figure 43:
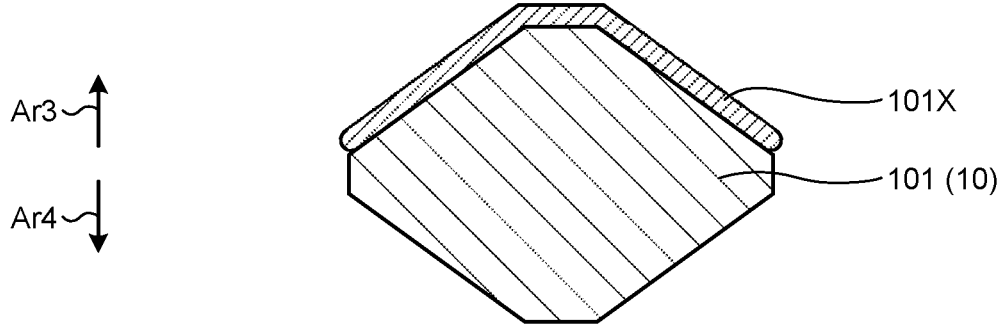
FIG. 43 is a view illustrating Modification 7-11 of the first to sixth embodiments.

FIG. 43 is a view illustrating Modification 7-11 of the first to sixth embodiments. Specifically, FIG. 43 is a cross-sectional view of the treatment portion 101 taken along a plane orthogonal to the central axis Ax.

In the above-described first embodiment, as in the present Modification 7-11 illustrated in FIG. 43, a processed portion 101X may be provided on the surface of the treatment portion 101. In the other second to sixth embodiments as well, the processed portion 101X may be provided on the surface of the treatment portion 101.

The processed portion 101X is provided at a position facing the gripping surface 911 on the surface of the treatment portion 101. The processed portion 101X is made of a material of which relative wear between the processed portion 101X and the resin pad 9 is smaller than that of the treatment portion 101. Specifically, in a case where the treatment portion 101 is made of a titanium alloy, as the material of the processed portion 101X, carbon steel, cast iron, bronze, and the like can be exemplified.

According to the present Modification 7-11 described above, the following effects are obtained.

In the structure of the present Modification 7-11, the treatment portion 101 is provided with the processed portion 101X described above. Therefore, frictional heat generated in the resin pad 9 (gripping surface 911) by application of ultrasonic vibration can be reduced.

Modification 7-12 of First to Sixth Embodiments

In the above-described Modification 7-10, the processed portion 101X is made of a material different from that of the treatment portion 101, but the disclosure is not limited thereto. For example, the processed portion 101X may be formed by reducing a surface roughness of the treatment portion 101 by surface treatment. Here, the surface roughness of the processed portion 101X is preferably 0.5 μm to 4.0 μm.

Even in a case where the structure of the present Modification 7-12 described above is adopted, the same effects as those of the above-described Modification 7-11 are obtained.

Modification 7-13 of First to Sixth Embodiments

In the above-described first embodiment, the wiper jaw 82 and the arm 81, and the arm 81, and the sheath 7 may be coupled by a flexible wire material having thermal conductivity. In the other second to sixth embodiments as well, the wire material may be adopted.

According to the present Modification 7-13 described above, the following effects are obtained.

In the structure of the present Modification 7-13, the above-described wire material is adopted. For this reason, the heat of the resin pad 9 can be moved to the arm 81 side and the sheath 7 side by the wire material, and the dissipation efficiency of heat from the resin pad 9 can be improved.

Modification 7-14 of First to Sixth Embodiments

Figure 44:
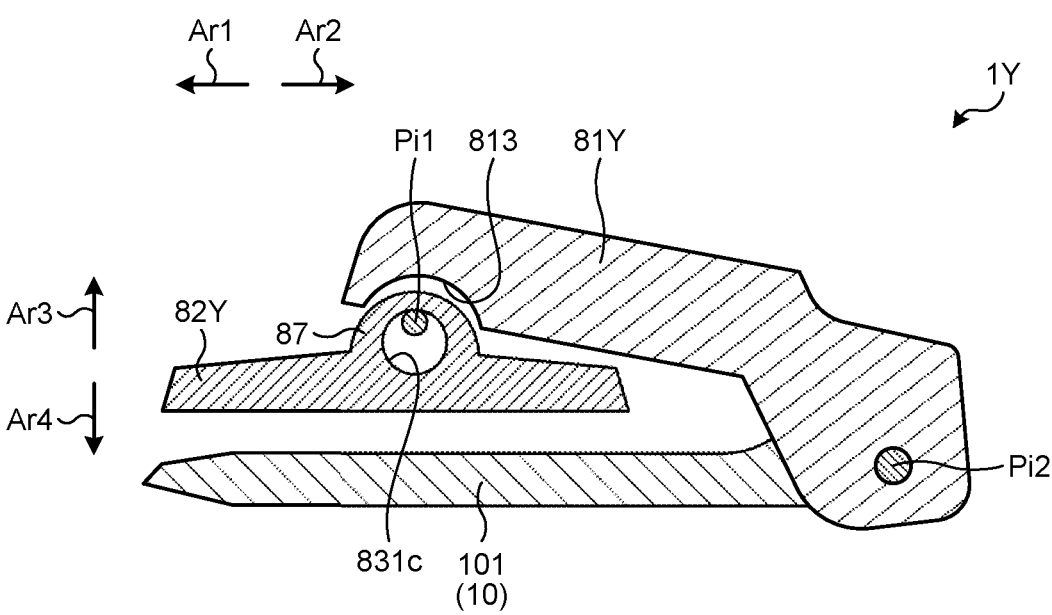
FIG. 44 is a view illustrating Modification 7-14 of the first to sixth embodiments.
Figure 45:
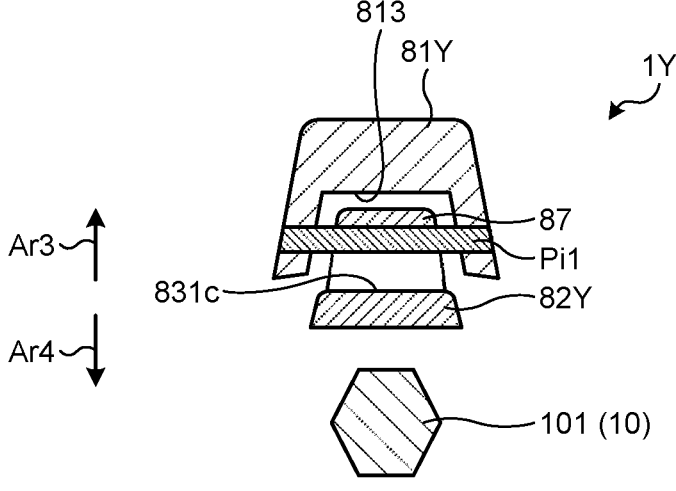
FIG. 45 is a view illustrating Modification 7-14 of the first to sixth embodiments.
Figure 46:
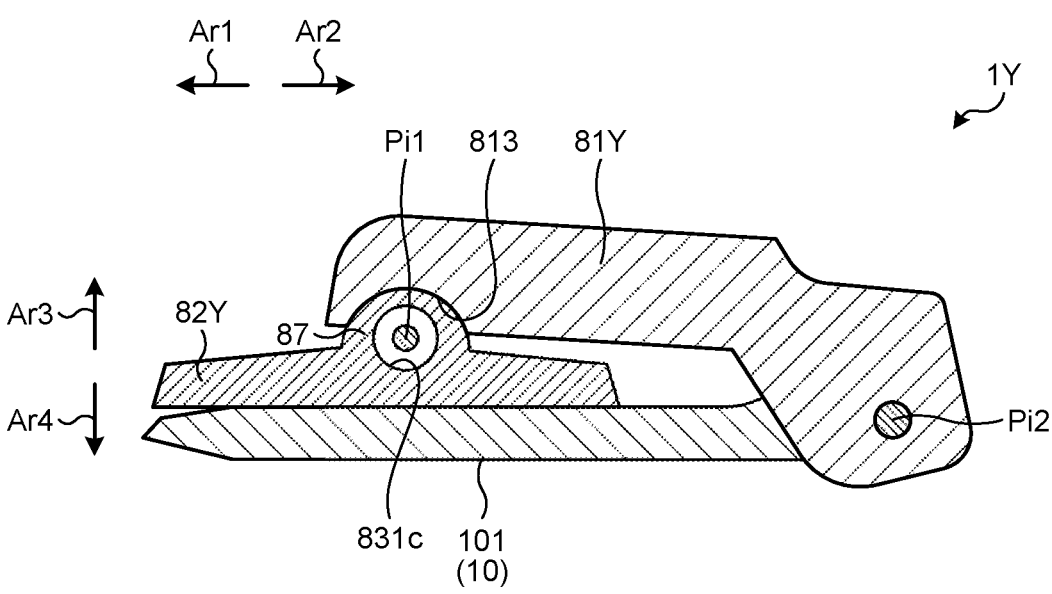
FIG. 46 is a view illustrating Modification 7-14 of the first to sixth embodiments.
Figure 47:
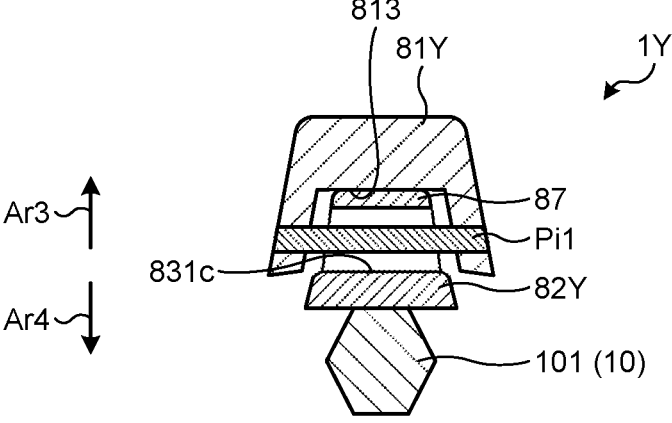
FIG. 47 is a view illustrating Modification 7-14 of the first to sixth embodiments.

FIGS. 44 to 47 are views illustrating Modification 7-14 of the first to sixth embodiments. Specifically, FIGS. 44 and 46 are cross-sectional views obtained by cutting a distal end portion of an ultrasonic treatment instrument 1Y according to the present Modification 7-14 along a plane orthogonal to the width direction. FIGS. 45 and 47 are cross-sectional views of the distal end portion of the ultrasonic treatment instrument 1Y taken along a plane passing through the fifth insertion hole 831c and orthogonal to the central axis Ax. FIGS. 44 and 45 illustrate a state in which the jaw 8 is opened with respect to the treatment portion 101. On the other hand, FIGS. 46 and 47 illustrate a state in which the jaw 8 is closed with respect to the treatment portion 101. In addition, in FIGS. 44 to 47, illustration of the resin pad 9 and the resin cover RC is omitted for convenience of description.

In the above-described first embodiment, as illustrated in FIGS. 44 to 47, the shapes of the arm 81 and the wiper jaw 82 may be changed as in the ultrasonic treatment instrument 1Y according to the present Modification 7-14. The same applies to the other second to sixth embodiments. Hereinafter, for convenience of description, the arm 81 and the wiper jaw 82 according to the present Modification 7-14 are referred to as an arm 81Y and a wiper jaw 82Y, respectively.

In the wiper jaw 82Y, the shape of the surface on the back surface side Ar3 is changed with respect to the wiper jaw 82 described in the above-described first embodiment.

Specifically, in the wiper jaw 82Y, the surface on the back surface side Ar3 is provided with a bulging portion 87 positioned on the back surface side Ar3 of the fifth insertion hole 831c and extending in the width direction.

As illustrated in FIG. 44 or 46, the bulging portion 87 has a semicircular cross-sectional shape centered on the central axis of the fifth insertion hole 831c.

In the arm 81Y, the shape of the surface of the treatment portion side Ar4 is changed with respect to the arm 81 described in the above-described first embodiment.

Specifically, in the arm 81Y, a groove portion 813 having an inner surface shape substantially the same as an outer surface shape of the bulging portion 87 is provided at a position facing the bulging portion 87 on the surface of the treatment portion side Ar4.

Then, in a state where the jaw 8 is closed with respect to the treatment portion 101, as illustrated in FIG. 46 or 47, the outer surface of the bulging portion 87 abuts on an inner surface of the groove portion 813 by the gripping pressure applied to the living tissue. On the other hand, in a state where the jaw 8 is opened with respect to the treatment portion 101, the outer surface of the bulging portion 87 is separated from the inner surface qof the groove portion 813 as illustrated in FIG. 44 or 45.

According to the present Modification 7-14 described above, the following effects are obtained.

In the structure of the present Modification 7-14, the groove portion 813 and the bulging portion 87 that abut on each other are provided by the gripping pressure applied to the living tissue. Therefore, the heat of the resin pad 9 can be moved to the arm 81Y side by the groove portion 813 and the bulging portion 87, and the dissipation efficiency of heat from the resin pad 9 can be improved.

Modification 7-15 of First to Sixth Embodiments

In the above-described first embodiment, the configuration in which both the ultrasonic energy and the high-frequency energy are applied to the target site is adopted, but the disclosure is not limited thereto. For example, a configuration of applying only ultrasonic energy to the target site or a configuration of applying at least one of high-frequency energy and thermal energy in addition to ultrasonic energy to the target site may be adopted. Here, applying thermal energy to the target site means transferring heat of a heater or the like to the target site. The same applies to the other second to sixth embodiments.

Modification 7-16 of First to Sixth Embodiments

In the above-described first to sixth embodiments, as the holder, a configuration including the arm 81 and the wiper jaw 82 swingably attached to the arm 81 is adopted, but the disclosure is not limited thereto. The holder may be openable and closable with respect to the treatment portion 101, and a configuration in which the wiper jaw 82 is not provided may be adopted.

According to an ultrasonic treatment instrument of the disclosure, deterioration of the resin pad can be suppressed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment instrument comprising:
   a rod configured to transmit ultrasonic vibration from a proximal end of the rod toward a distal end of the rod;
   a holder facing the rod;
   a resin pad located in the holder, wherein the resin pad is configured to grip a living tissue with the rod; and
   a sheet made of thermally conductive material disposed between the holder and the resin pad, wherein the sheet is configured to transfer heat from the resin pad to the holder, and wherein the sheet is an adhesive or a heat sealing sheet.

2. The ultrasonic treatment instrument according to claim 1, wherein the sheet is a graphite sheet.

3. The ultrasonic treatment instrument according to claim 1, wherein the sheet contains any one of boron nitride, alumina, metal powder, carbon nanotube, and silicon carbide.

4. The ultrasonic treatment instrument according to claim 1, wherein the resin pad is provided with a plurality of holes along a longitudinal direction of the resin pad, and the sheet is configured to enter the plurality of holes.

5. The ultrasonic treatment instrument according to claim 1, wherein the resin pad is provided with a groove portion, and the sheet is provided with a protrusion fitted into the groove portion.

6. The ultrasonic treatment instrument according to claim 1, wherein the holder includes a top wall, wherein the resin pad includes a grasping surface facing the rod and a top surface opposed to the grasping surface and facing the top wall, and wherein the sheet is located between the top wall and the top surface.

7. The ultrasonic treatment instrument according to claim 1, wherein the holder includes a top wall and a wall surface intersecting with the top wall, wherein the resin pad includes a grasping surface facing the rod and a side surface, wherein the side surface intersects with the grasping surface and faces a side wall, and wherein the sheet is located between the side wall and the side surface.

8. The ultrasonic treatment instrument according to claim 1, wherein the sheet is formed from a material having a higher thermal conductivity than the resin pad.

9. The ultrasonic treatment instrument according to claim 1, wherein the sheet is configured to dissipate heat of the resin pad.

10. An ultrasonic treatment instrument comprising:
a vibration transmitter including a treatment portion for treating a living tissue at a distal end of the vibration transmitter, wherein the vibration transmitter is configured to transfer ultrasonic vibration from a proximal end of the vibration transmitter toward the treatment portion;
a holder configured to open and close with respect to the treatment portion;
a resin pad including a gripping surface for gripping the living tissue between the resin pad and the treatment portion; and
a heat transmitter disposed between the holder and the resin pad, wherein heat transmitter is a graphite sheet.

11. An ultrasonic treatment instrument comprising:
a vibration transmitter including a treatment portion for treating a living tissue at a distal end of the vibration transmitter, wherein the vibration transmitter is config-ured to transfer ultrasonic vibration from a proximal end of the vibration transmitter toward the treatment portion;
a holder configured to open and close with respect to the treatment portion;
a resin pad including a gripping surface for gripping the living tissue between the resin pad and the treatment portion; and
a heat transmitter disposed between the holder and the resin pad wherein the resin pad is provided with a plurality of holes along a longitudinal direction of the resin pad, and the heat transmitter is configured to enter the plurality of holes.

* * * * *